(12) United States Patent
C.Y. Chang et al.

(10) Patent No.: US 9,049,856 B2
(45) Date of Patent: Jun. 9, 2015

(54) COLD ORGAN PRESERVATION COMPOSITION AND METHOD OF USE

(75) Inventors: Haisul C.Y. Chang, Navarra (ES); Victor Fernández Gallego, Navarra (ES); María Iñiguez Martínez, Navarra (ES); Jose Miguel López Novoa, Navarra (ES); Jesús María Prieto Valtueña, Navarra (ES); Juan Ruiz Echeverría, Navarra (ES)

(73) Assignees: DIGNA ATOTECH, S. L., Pamplona (Navarra) (ES); PROYECTO DE BIOMEDICINE CIMA, S.L., Pamplona (Navarra) (ES)

( * ) Notice: Subject to any disclaimer, the term of this patent is extended or adjusted under 35 U.S.C. 154(b) by 0 days.

(21) Appl. No.: 13/699,792

(22) PCT Filed: May 24, 2011

(86) PCT No.: PCT/ES2011/070375
§ 371 (c)(1),
(2), (4) Date: Jan. 22, 2013

(87) PCT Pub. No.: WO2011/148024
PCT Pub. Date: Dec. 1, 2011

(65) Prior Publication Data
US 2013/0130225 A1   May 23, 2013

(30) Foreign Application Priority Data
May 24, 2010   (ES) .................... 201030782

(51) Int. Cl.
*A01N 1/00*   (2006.01)
*A01N 1/02*   (2006.01)

(52) U.S. Cl.
CPC ............ *A01N 1/0221* (2013.01); *A01N 1/0226* (2013.01)

(58) Field of Classification Search
USPC .......................................................... 435/1.2
IPC .................................................... A01N 1/0221
See application file for complete search history.

(56) References Cited

U.S. PATENT DOCUMENTS

| | | | |
|---|---|---|---|
| 4,798,824 A | 1/1989 | Belzer et al. | |
| 4,879,283 A | 11/1989 | Belzer et al. | |
| 5,208,145 A * | 5/1993 | Rogers | 435/6.16 |

OTHER PUBLICATIONS

Belzer et al. The Use of UW Solution in Clinical Transplantation; Annals of Surgery, vol. 216, No. 6 (1992) pp. 579-583.*
Nunes et al. Efficacy of Renal Preservation: Comparative Study of Celsior and University of Wisconsin Solutions; Transplantation Proceedings, vol. 39 (2007) pp. 2478-2479.*
European Medicines Agency Public Summary of Opinion on Orphan Designation; (Jun. 11, 2010) downloaded from http://www.ema.europa.eu/docs/en_GB/document_library/Orphan_designation/2009/10/WC500005935.pdf.*
Chica et al. Semi-Rational Approaches to Engineering Enzyme Activity: Combining the Benefits of Directed Evolution and Rational Design; Current Opinion in Biotechnology, vol. 16 (2005) pp. 378-384.*
Witkowski et al. Conversion of a Beta-Ketoacyl Synthase to a Molonyl Decarboxylase by Replacement of the Active-Site Cysteine With Glutamine; Biochemistry, vol. 38 (1999) pp. 11643-11650.*
Whisstock et al. Prediction of Protein Function From Protein Sequence and Structure; Quarterly Reviews of Biophysics, vol. 36, No. 3 (2003) pp. 307-340.*
Calhoon et al. Twelve-Hour Canine Heart Preservation With a Simple, Portable Hyperthermic Organ Perfusion Device; Annals of Thoracic Surgery, vol. 62 (1996) pp. 91-93.*
Ahmad N., et al., "Comparative efficacy or renal preservation solutions to limit functional impairment after warm ischemic injury", Kidney International, 2006, vol. 69, pp. 884-893.
Belzer, FO. and Southard JH., "Principles of solid-organ preservation by cold storage", Transplantation, 1988, vol. 45, pp. 673-676.
Ben, Abdennebi H, et al., "A preservation solution with polyethylene glycol and calcium: a possible multiorgan liquid", Transplantation Int., 2002, vol. 15, pp. 348-354.
Bretschneider, HJ, "Myocardial protection", Thorac Cardiovasc Surgeon, 1980, vol. 28, pp. 295-302.
Chen, F, et al. "Development of new organ preservation solutions in Kyoto University", Yonsie Medical Journal, 2004, vol. 45, p. 1107-1114.
Collins G.M., et al. "Kidney preservation for transportation", The Lancet 1969, vol. 2, pp. 1219-1222.
El-Wahsh, M. "Liver graft preservation and overview", Hepatobiliary Pancreat Dis Int., 2007, vol. 6(1), pp. 12-16.
Garcia-Criado, et al. "Protective effect of new nitrosothiols on the early inflammatory response to kidney ischemia/reperfusion and transplantation in rats", Journal of Interferon & Cytokine Research, 2009, vol. 29. pp. 441-449.
Hausenloy, D.J. and Yellon D.M., "New directions for protecting the heart against ischaemia-reperfusion injury; targeting the reperfusion injury salvage kinase (RISK) pathway", Cardiovascular Research, 2004, vol. 61, pp. 448-460.
Herrero-Fresneda, et al. "Role of cold ischemic in acute rejection: characterization of a humoral-like acute rejection in experimental renal transplantation", Transplantation Proceedings, 2005, vol. 37, pp. 3712-3715.
Iñiquez M. et al. "Cardiotrophin-1 defends the live against ischemia-reperfusion injury and mediates the protective effect of ischemic preconditioning", The Journal of Experimental Medicine, 2006, vol. 203., No. 13 pp. 2809-2815.

(Continued)

*Primary Examiner* — Sharmila G. Landau
*Assistant Examiner* — Paul Martin
(74) *Attorney, Agent, or Firm* — Gary J. Gershik; Cooper & Dunham LLP

(57) ABSTRACT

The present invention relates to a cold organ preservation composition for transplantation comprising a cold organ preservation solution and cardiotrophin-1 or a functionally equivalent variant thereof. The invention also relates to methods and kits for the preparation of said composition, the uses thereof for the cold organ protection and/or preservation for transplantation (particularly for kidney, lung and heart) and also to the cold preservation methods and cold-preserved isolated organs by these methods.

15 Claims, 23 Drawing Sheets

(56) References Cited

OTHER PUBLICATIONS

Lam F.T., et al. "Improved 72-hour renal preservation with phosphate-buffered sucrose", Transplantation, 1989, vol. 47, pp. 767-771.

Liao Z., et al. "Cardiotrophin-1 (CT-1) can protect the adult heart from injury when added both prior to ischaemia and at reperfusion", Cardiovascular Research, 2002, vol. 53, pp. 902-910.

Maathuis M-H, et al. "Perspectives in organ preservation", Transplantation, 2007, vol. 83, pp. 1289-1298.

Menasché P., et al. "Experimental evaluation of celsior®, a new heart preservation solution", Eur. J. Cardio-thorac Surg., 1994, vol. 8, pp. 207-213.

Michel P., et al. "A comparative study of the most widely used solutions for cardiac graft preservation during hypothermia", J Heart & Lung Transplant, 2002, vol. 21, pp. 1030-1039.

Michel P., et al. "Evaluation of new preservation solution for cardiac graft during hypothermia", J Heart & Lung Transplantation, 2000, vol. 19, pp. 1089-1097.

Müller, C., et al. "Lung procurement by low-potassium dextran and the effect of preservation injury", Transplantation, 1999, vol. 68. pp. 1139-1143.

Salahudeen, A.K., "Cold ischemic injury of transplanted kidneys: new insights from experimental studies", Am. J. Physiol, Renal Physiol, 2004, vol. 287, pp. F181-F187.

Southard J.H. and Belzer FO, "Organ preservation", Annu. Rev. Med., 1995, vol. 46, pp. 235-247.

Wei, L., et al. "Experimental small bowel preservation using polysol: a new alternative to University of Wisconsin solution, celsior and histidine-tryptophan-ketoglutarate solution", World J. Gastroenterol, 2007, vol. 13(27), pp. 3684-3691.

Ahlsson, A., et al. "Adenosine in cold Blood Cardioplegia—a Placebo-controlled Study", Interactive CardioVascular and Thoracic Surgery, 2012, vol. 14, pp. 48-55.

Liu, S.Q. et al. "Cardioprotective Mechanisms Activated in Response to Myocardial Ischemia", MCB, 2011, vol. 8, pp. 319-338.

Privalov, P.L., "Cold Denaturation of Proteins", Biochemistry and Molecular Biology, 1990, vol. 25(4), pp. 281-306.

\* cited by examiner

C   iNOS

D   IκB

A

B

E

F

I

J

SEQUENCE LISTING

<160> NUMBER OF SEQ ID NOS: 2

<210> SEQ ID NO 1
<211> LENGTH: 201
<212> TYPE: PRT
<213> ORGANISM: Homo sapiens

<400> SEQUENCE: 1

Met Ser Arg Arg Glu Gly Ser Leu Glu Asp Pro Gln Thr Asp Ser Ser

```
 1               5                   10                  15
Val Ser Leu Leu Pro His Leu Glu Ala Lys Ile Arg Gln Thr His Ser
            20                  25                  30
Leu Ala His Leu Leu Thr Lys Tyr Ala Glu Gln Leu Leu Gln Glu Tyr
            35                  40                  45
Val Gln Leu Gln Gly Asp Pro Phe Gly Leu Pro Ser Phe Ser Pro Pro
            50                  55                  60
Arg Leu Pro Val Ala Gly Leu Ser Ala Pro Pro Ser His Ala Gly
 65                 70                  75                  80
Leu Pro Val His Glu Arg Leu Arg Leu Asp Ala Ala Leu Ala Ala
                85                  90                  95
Leu Pro Pro Leu Leu Asp Ala Val Cys Arg Arg Gln Ala Glu Leu Asn
            100                 105                 110
Pro Arg Ala Pro Arg Leu Leu Arg Arg Leu Glu Asp Ala Ala Arg Gln
            115                 120                 125
Ala Arg Ala Leu Gly Ala Ala Val Glu Ala Leu Leu Ala Ala Leu Gly
            130                 135                 140
Ala Ala Asn Arg Gly Pro Arg Ala Glu Pro Pro Ala Ala Thr Ala Ser
145                 150                 155                 160
Ala Ala Ser Ala Thr Gly Val Phe Pro Ala Lys Val Leu Gly Leu Arg
                165                 170                 175
Val Cys Gly Leu Tyr Arg Glu Trp Leu Ser Arg Thr Glu Gly Asp Leu
            180                 185                 190
Gly Gln Leu Leu Pro Gly Gly Ser Ala
            195                 200

<210> SEQ ID NO 2
<211> LENGTH: 239
<212> TYPE: PRT
<213> ORGANISM: Artificial Sequence
<220> FEATURE:
<223> OTHER INFORMATION: recombinant rat cardiotrophin-1

<400> SEQUENCE: 2

Met Arg Gly Ser His His His His His His Gly Met Ala Ser Met Thr
 1               5                  10                  15
Gly Gly Gln Gln Met Gly Arg Asp Leu Tyr Asp Asp Asp Lys Asp
            20                  25                  30
Arg Trp Gly Ser Met Ser Gln Arg Glu Gly Ser Leu Glu Asp His Gln
            35                  40                  45
Thr Asp Ser Ser Phe Ser Phe Leu Pro His Leu Glu Ala Lys Ile Arg
            50                  55                  60
Gln Thr His Asn Leu Ala Arg Leu Leu Thr Lys Tyr Ala Asp Gln Leu
 65                 70                  75                  80
Leu Glu Glu Tyr Val Gln Gln Gly Glu Pro Phe Gly Leu Pro Gly
                85                  90                  95
Phe Ser Pro Pro Arg Leu Pro Leu Ala Gly Leu Ser Gly Pro Ala Pro
            100                 105                 110
Ser His Ala Gly Leu Pro Val Ser Glu Arg Leu Arg Gln Asp Ala Ala
            115                 120                 125
Ala Leu Ser Ala Leu Pro Ala Leu Leu Asp Ala Val Arg Arg Arg Gln
            130                 135                 140
Ala Glu Leu Asn Pro Arg Ala Pro Arg Leu Leu Arg Ser Leu Glu Asp
145                 150                 155                 160
Ala Ala Arg Gln Val Arg Ala Leu Gly Ala Ala Val Glu Thr Val Leu
```

-continued

```
                165                 170                 175
Ala Ala Leu Gly Ala Ala Ala Arg Gly Pro Val Pro Glu Pro Val Ala
            180                 185                 190

Thr Ser Ala Leu Phe Thr Ser Asn Ser Ala Ala Gly Val Phe Ser Ala
        195                 200                 205

Lys Val Leu Gly Leu His Val Cys Gly Leu Tyr Gly Glu Trp Val Ser
    210                 215                 220

Arg Thr Glu Gly Asp Leu Gly Gln Leu Val Pro Gly Gly Val Ala
225                 230                 235
```

COLD ORGAN PRESERVATION COMPOSITION AND METHOD OF USE

TECHNICAL FIELD OF THE INVENTION

The present invention relates to a cold organ preservation composition for transplantation and to the uses, methods and kits for the preparation thereof.

BACKGROUND OF THE INVENTION

Organ transplantation is extensively used for organs such as the heart, the lung, the pancreas, the intestine (colon) and, in particular, the kidney and the liver. The growing demand of organs and the scarcity of donours have led to a growing waiting list and a greater need to use organs from sub-optimal donours.

Organs obtained for transplantation must be stored and transported from one hospital to another. Time is needed to test the histocompatibility between donour and recipient, and to prepare the recipient patient. The time period during which organs and tissues may be maintained outside the body varies, depending on the organ, the donour's age and health condition, the preservation method and the temperature.

Currently, the standard technique used in clinical practise to prolong the viability of donated organs is cold storage or cold preservation, by means of special preservation solutions. These solutions are used in a first stage, prior to the extraction, for a perfusion (flushing) of the organ designed to remove and replace the donour's blood, whilst cooling it to 4° C. In a second stage, the cold preservation solutions are used to store and preserve the extracted organ, also under hypothermia (about 4° C.), until transplantation. The purpose of cold preservation is to preserve the organ by means of a suppression of metabolism and, in the second place, to prevent and minimise the alterations that cold ischaemia might cause.

Maathuis et al. (Transplantation, 2007; 83: 1289-1298) provide a recent review of cold preservation solutions which discloses the general requirements, as well as the composition and the properties of a large number thereof, such as the Euro-Collins solution (EC). Marshall's hypertonic citrate solution (HOC), sucrose phosphate buffer, the University of Wisconsin solution (UW), the histidine-tryptophan-ketoglutarate (HTK) solution, the Celsior solution (CEL), the Institut Georges López solution (IGL-1). There are comparative studies on the efficacy of some of these solutions on the preservation of the kidney (Ahmad et al. Kidney International 2006; 69: 884-893), the heart (Michel et al. J. Heart Lung Transplant 2002; 21: 1030-1039), the liver (El-Wahsh M. Hepatobiliary Pancreat Dis Int 2007; 6: 12-16) and the intestine (Wei et al. Gastroenterology 2007; 13:3n84-3091), The most commonly used cold preservation solutions are the University of Wisconsin solution, in particular for the liver and the kidney; the Celsior solution for heart preservation; and Euro-Collins or PERFADEX™ for lung preservation. In the case of perfusion machines, these have been modified, for example to UW-gluconate (Belzer MPS).

U.S. Pat. No. 4,798,824 discloses a cold preservation solution that comprises gluconate and hydroxyethyl starch. U.S. Pat. No. 4,879,283 discloses the University of Wisconsin solution (UW or Belzer solution), which comprises the following differential components: lactobionate and raffinose, as impermeating agents designed to reduce cellular swelling; and hydroxyethyl starch, in order to prevent edema.

However, cold preservation with the current preservation solutions has significant limitations. The tissue damage and the inflammatory response caused by cold preservation may increase immunogenicity and initiate rejection of the organ. Thus, for example, in experimental models of kidney transplantation with rejection, cold ischaemia contributed to an increase in the mortality rate due to kidney failure and an accelerated acute rejection (Salahudeen A K. Am J Physiol Renal Physiol. 2004; 287: F181-F187; Herrero-Fresneda et al. Transplant Proc. 2005; 37: 3712-3715).

Cold ischaemia is related to alterations of osmoregulation, energy and the aerobic metabolism. A reduction in Na—K-ATPase activity and ATP levels allows for an intracellular accumulation of sodium and water, thereby causing cellular swelling. Likewise, the lactic acid produced by glucose metabolism leads to lysosomal instability and alteration of the mitochondrial function, causing swelling, activation of the mitochondrial apoptotic pathway and production of free radicals.

On the other hand, once the transplantation has been performed, a new damage is added, caused by re-perfusion of the organ, which is possibly more sensitive due to the cold ischaemia whereto it has been subjected. The following are involved in this damage process: an increase in reactive oxygen free radicals, in the inflammatory response and the cytosolic calcium, as well as an activation of proteolytic enzymes, for example, caspases.

Consequently, there is a need in the state of the art to provide an adequate cold organ preservation composition that makes it possible to reduce the damages associated with cold ischaemia and the post-transplantation reperfusion of cold-preserved organs.

SUMMARY OF THE INVENTION

A first aspect of the invention relates to a cold organ preservation composition that comprises, jointly or separately,
(i) cardiotrophin-1 (CT-1) or a functionally equivalent variant thereof, and
(ii) a cold organ preservation solution, Another aspect of the invention relates to a method of preparing a cold organ preservation composition, which comprises adding cardiotrophin-1 or a functionally equivalent variant thereof to a cold organ preservation solution.

Another aspect of the invention relates to the use of cardiotrophin-1 or a functionally equivalent variant thereof for the preparation of a cold organ protection and/or preservation composition for transplantation.

Yet another aspect of the invention relates to the use of a composition in accordance with the invention for cold organ protection and/or preservation for transplantation.

Another aspect of the invention relates to a cold organ preservation composition in accordance with the invention for use in the cold organ protection and/or preservation for transplantation.

Another aspect of the invention also relates to a method for the cold preservation of an organ, which comprises contacting said organ with a composition in accordance with the invention.

Another aspect of the invention relates to a cold-preserved isolated organ obtained by means of a method of the invention.

A final aspect of the invention relates to a kit designed for the preparation of a cold organ preservation composition, which comprises:
(i) cardiotrophin-1 or a functionally equivalent variant thereof; and (ii) a cold organ preservation solution or, alternatively, media and additives for the preparation of said solution.

DETAILED DESCRIPTION OF THE INVENTION

The authors of the present invention have surprisingly observed that the addition of cardiotrophin-1 (CT-1) to cold organ preservation solutions makes it possible to obtain adequate cold organ preservation compositions, (especially for the kidneys, lungs and heart), which reduce the damages associated with cold ischaemia and post-transplantation reperfusion in said organs. Said effect is dependent on the capacity of the compositions of the invention to:

reduce the oxidative stress caused, by decreasing the production of oxygen free radicals (FIGS. 1A, 2A, 5D and 6D);

reduce the activation of inflammatory responses, by preventing the activation of pro-inflammatory signalling pathways (NFκB) (FIGS. 1D and 2D), reducing the production of inflammatory cytokines (TNFα, iNOS, IL-6) (FIGS. 1B-C, 2B-C, 4F, 5A and 7) and pro-inflammatory adhesion molecules (VCAM-1, ICAM-1) (FIGS. 3F and 4H-I).

Another objective of the present invention is to provide an adequate cold organ preservation composition for transplantation which improves the viability of solid organ transplantation and the survival rates.

Figure 4:
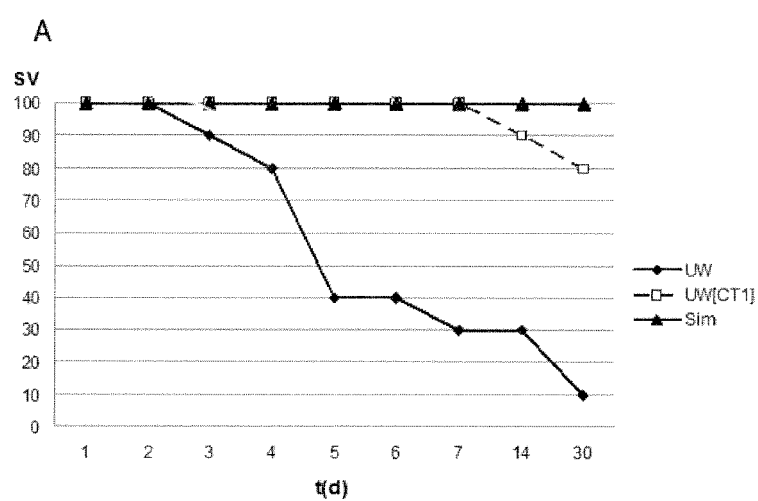
FIG. 4. Study of the effect on the kidney of cold preservation with a UW solution that contains 0.1 mg/l of CT-1 (UW [CT1]) and with the University of Wisconsin solution (UW) used as a control, in an experimental model of homologous and orthotopic kidney transplantation in rats. The pre-set reperfusion times for the different groups were, respectively, in days t(d): 1, 3, 7 and 14. A simulated group of rats was also included (Sim). n>15 transplantations per group. A) Survival, expressed as the % of live rats with respect to the total. B) Serum levels of creatinine (CREAT), expressed in mg/dl. C) Creatinine clearance levels (CRCL), expressed in relative units. D) Renal levels of the superoxide anion free radical (SOA), expressed in nmol/mg protein/minute. E) Renal levels of tumour necrosis factor alpha (TNFα), expressed in pg/ml. F) Renal levels of interleukin-6 (IL-6), expressed in pg/ml. G) Activation of the NFκB transcriptional factor measured by the levels of renal IκB (IκB), expressed in arbitrary units. H) Levels of the soluble form of the ICAM-1 adhesion molecule (sICAM-1). I) Levels of the soluble form of the VCAM-1 adhesion molecule (sVCAM-1).
Figure 4:
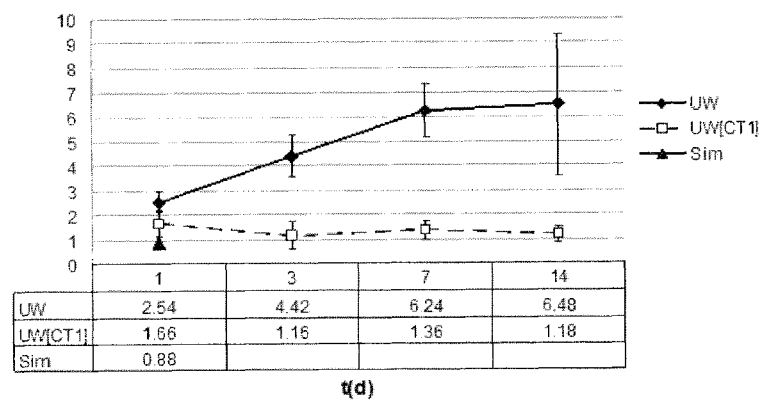
Figure 4:
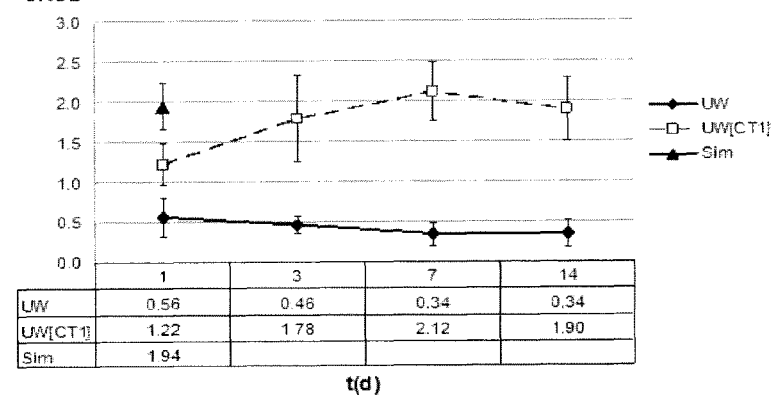
Figure 4:
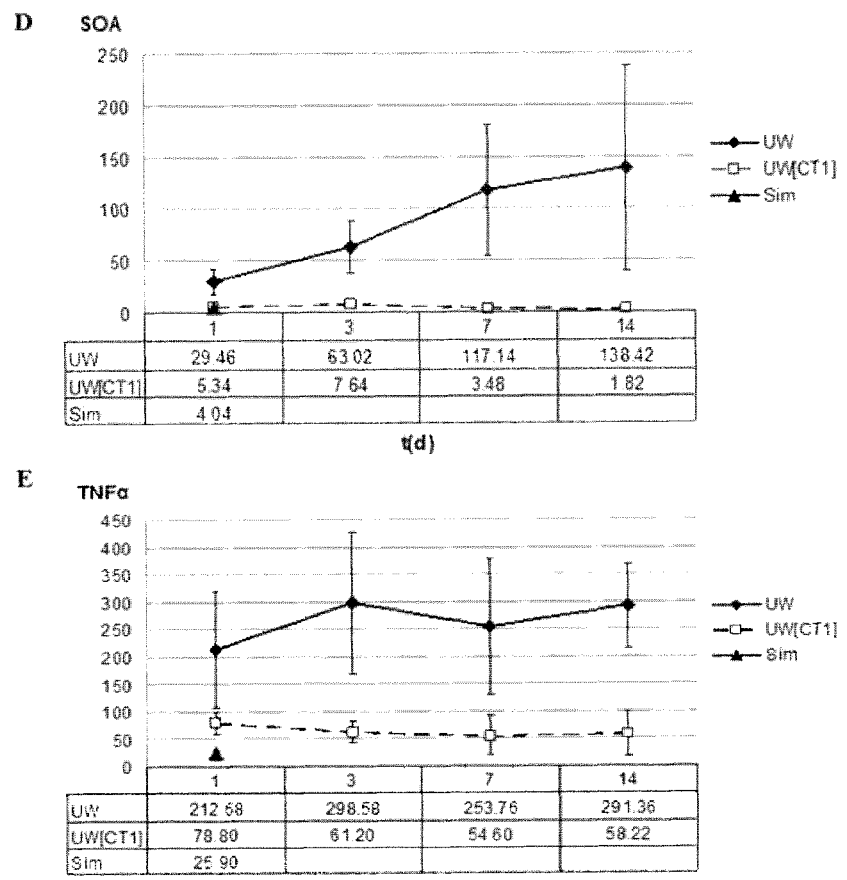
Figure 4:
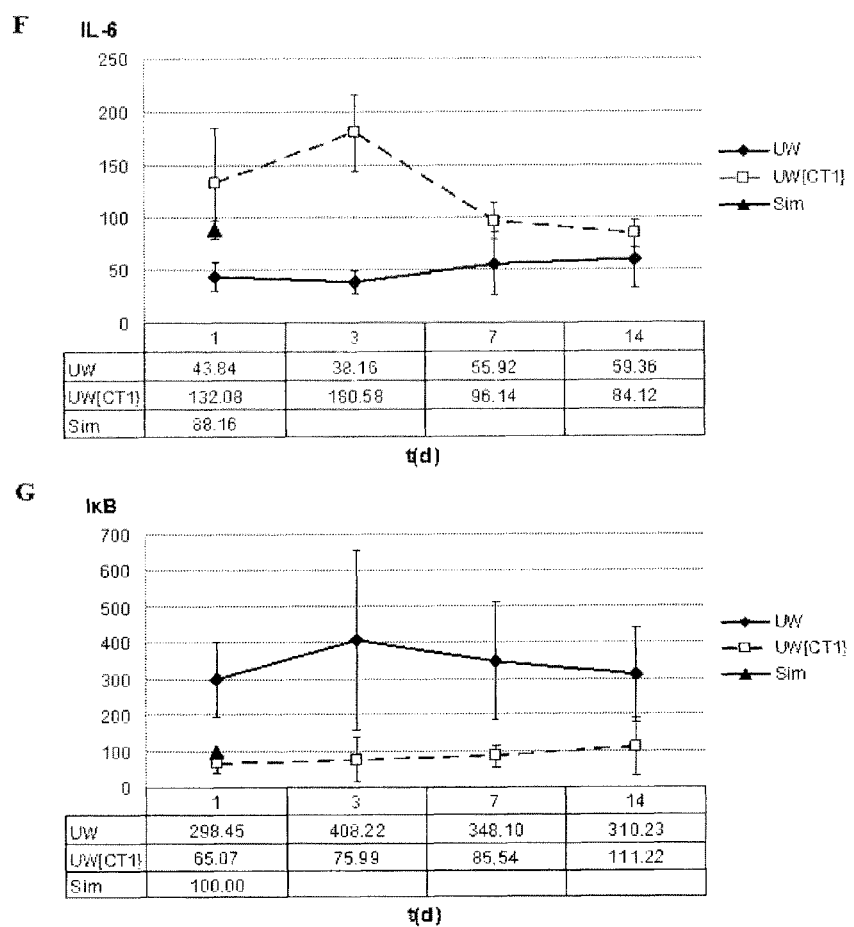
Figure 4:
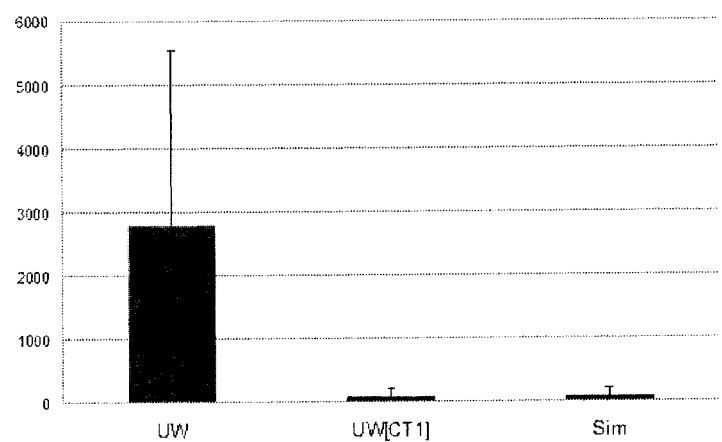
Figure 4:
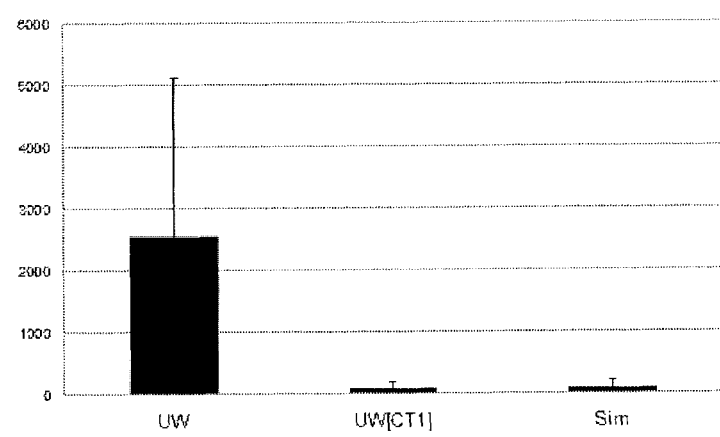
Figure 5:
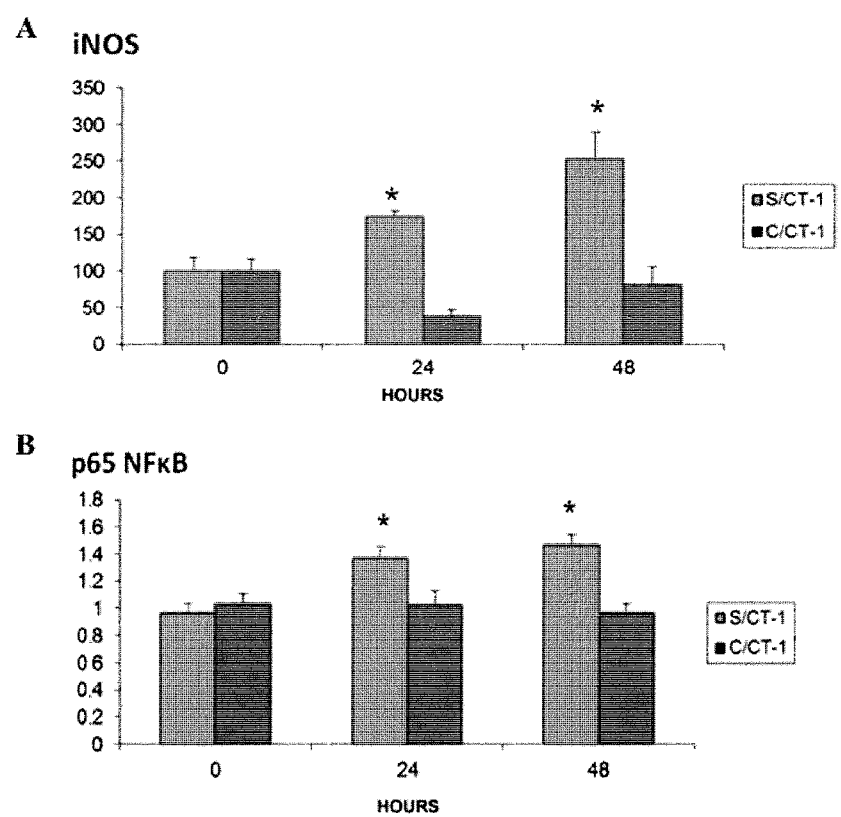
FIG. 5. Comparative study of the effect of the cold preservation (4° C.) in the lungs of Wistar rats of the University of Wisconsin solution (S/CT-1) and the University of Wisconsin solution with 0.2 mg/L of CT-1 (C/CT-1) at different times expressed in hours. n=5 animals per group. A) Inducible nitric oxide synthase (iNOS) tissue levels, expressed in arbitrary units. *p<0.05 with respect to group 0, with or without CT-1. B) p65 or NFκB (p65 NFκB) protein tissue levels, expressed in arbitrary units. *p<0.05 with respect to group 0, with or without CT-1. C) Activation of the NFκB transcription factor measured by means of tissue levels of the Ser$^{311}$-phosphorylated p65 protein (pNFκB), expressed in arbitrary units. *p<0.05 with respect to group 0, with or without CT-1, and to group 48 with CT-1. D) Superoxide anion (SOA) free radical tissue levels, expressed in nmol/mg protein/minute.*p<0.05 with respect to group 0, 24 h and 48 h, with CT-1, and with respect to group 0, without CT-1.
Figure 5:
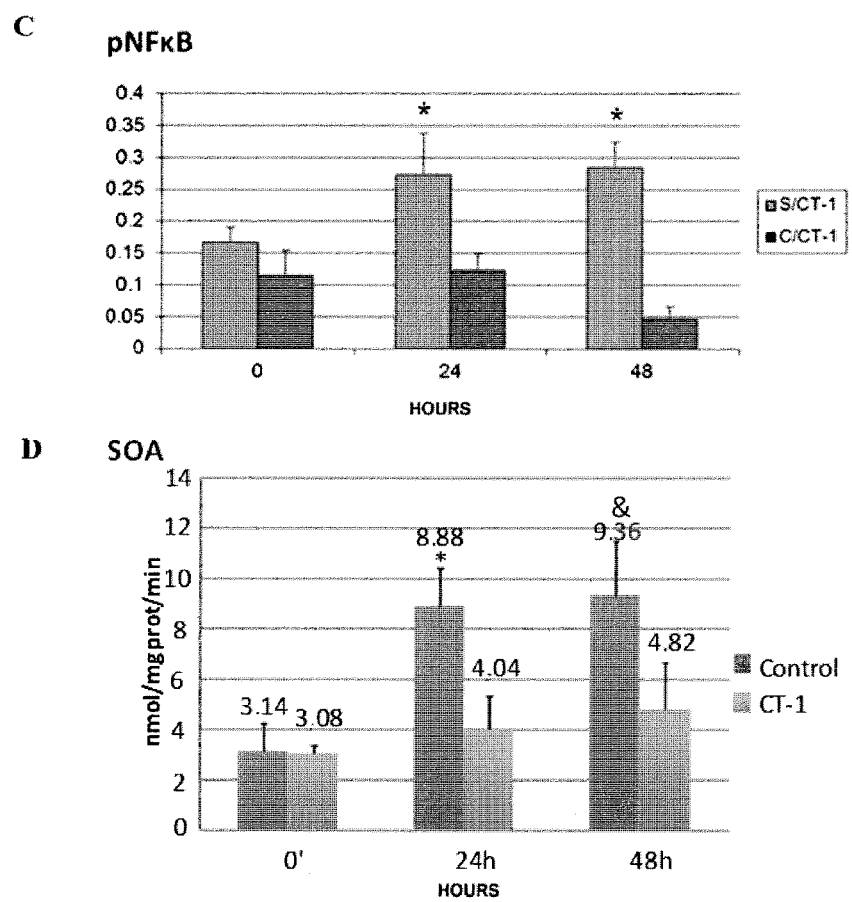
Figure 6:
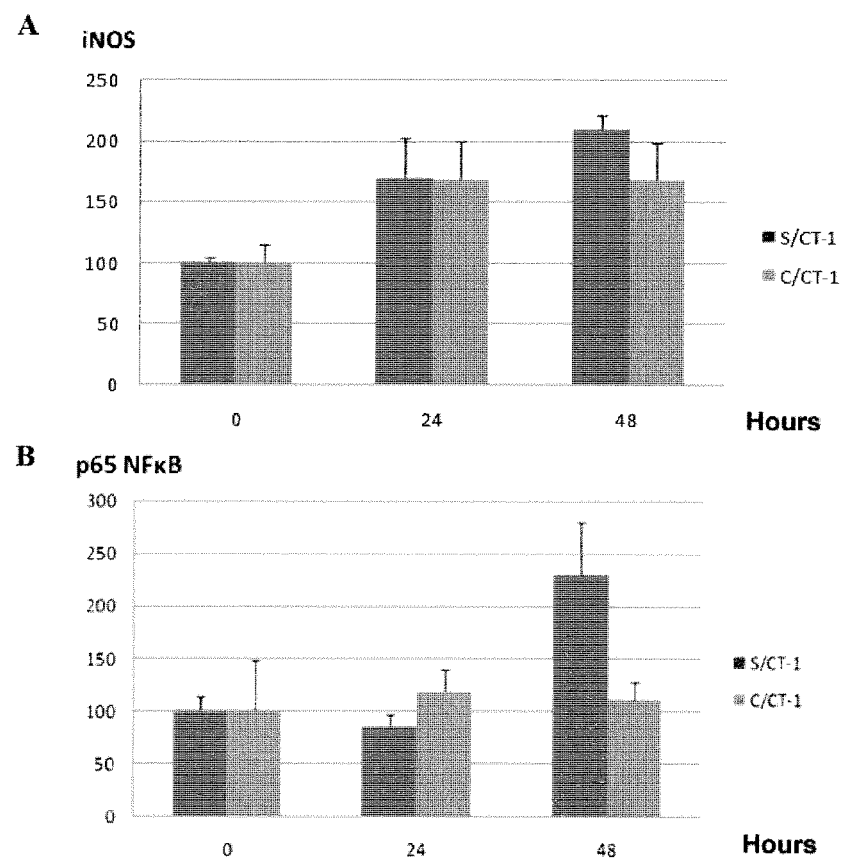
FIG. 6. Comparative study of the effect of the cold preservation (4° C.) in the heart of Wistar rats of the University of Wisconsin solution (S/CT-1) and the University of Wisconsin solution with 0.2 mg/L of CT-1 (C/CT-1) at different times expressed in hours. n=5 animals per group. A) Inducible nitric oxide synthase (iNOS) tissue levels, expressed in arbitrary units. B) Activation of the NFκB transcription factor measured by means of p65 NFκB tissue levels, expressed in arbitrary units. C) Tubulin-corrected soluble ICAM-1 adhesion molecule (sICAM-1) tissue levels, expressed in arbitrary units. D) Superoxide anion (SOA) free radical tissue levels, expressed in nmol/mg protein/minute. *p<0.05 with respect to group 0, 24 and 48 h, with CT-1, and with respect to group 0, without CT-1. & p<0.05 with respect to group 0, 24 and 48 h, with CT-1, and with respect to group 0, without CT-1.
Figure 6:
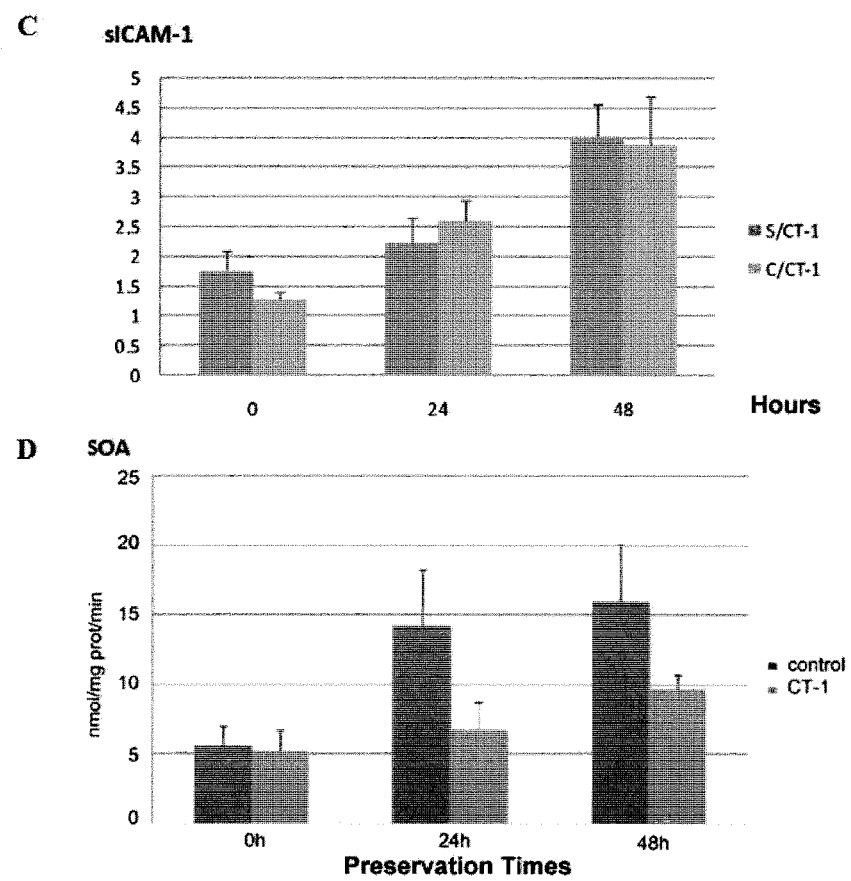

The authors of the present invention have additionally demonstrated that the compositions of the invention are suitable for the cold preservation of kidneys for transplantation, since they prevent the tubular necrosis caused by ischaemia-re-perfusion, thereby improving the renal function (reduction in the serum levels of creatinine and increase in creatinine clearance) and survival rates (FIG. 4).

Compositions of the Invention

Therefore, a first aspect of the invention relates to a cold organ preservation composition that comprises, jointly or separately, (i) cardiotrophin-1 (CT-1) or a functionally equivalent variant thereof and (ii) a cold organ preservation solution.

The term "cold organ preservation composition" or "composition designed for cold organ preservation", as used in this document, refers to a liquid composition, preferably sterile, that contains cardiotrophin-1 (or a functionally equivalent variant thereof) and a cold organ preservation solution. In said composition, CT-1 (or the functionally equivalent variant thereof) may be dispersed in the cold organ preservation solution, constituting a single formulation for joint use. Alternatively, the possibility is also considered that the composition of the invention comprises the two components, (i) and (ii), separately formulated, which in this case must be combined prior to the administration thereof.

The compositions in accordance with the invention are suitable compositions for cold organ preservation. "Cold organ preservation" is understood to mean the capacity to conserve, protect, preserve and/or store organs under hypothermic conditions, minimising cell damage in said organs, by using agents that produce a suppression of metabolism and prevent or counteract the alterations that cold ischaemia may cause in the organ. In the present invention, cardiotrophin-1 and the cold organ preservation solutions are suitable agents for cold organ preservation.

The term "cardiotrophin-1" or "CT-1", as used in the present invention, refers to a cytokine belonging to the interleukin-6 family that is capable of binding and activating the signalling mediated at least by the LIFR receptor complex consisting of the gp130/LIFRβ heterodimer. In the present invention, "CT-1" is understood to mean the protein defined by the NCBI database sequence with accession number NP_0013211, which corresponds to sequence SEQ ID NO: 1, corresponding to isoform 1 of human cardiotrophin; or the protein defined by the NCBI database sequence with accession number NP_001136016.1, corresponding to isoform 2 of human cardiotrophin. In a preferred embodiment. CT-1 is a CT-1 of human origin, preferably with sequence SEQ ID NO: 1.

```
                                                                    SEQ ID NO: 1
         MSRREGSLED PQTDSSVSLL PHLEAKIRQT HSLAHLLTKY AEQLLQEYVQ LQGDPFGLPS     60

FSPPRLPVAG LSAPAPSHAG LPVHERLRLD AAALAALTPL LDAVCRRQAE LNPRAPRLLR    120

RLEDAARQAR ALGAAVEALI AALGAANRGP RAEPPAATAS AASATGVFPA KVLGLRVCGL    180

YREWLSRTEG DLGQLLPGGS A                                              201
```

The invention considers the use of functionally equivalent variants of CT-1. "Functionally equivalent variant of CT-1", as used herein, is understood to mean any molecule that shares one or more of the functions described in the present invention as being associated with CT-1, both in vitro and in vivo, and exhibits a minimum identity in the amino acid sequence. The variants of CT-1 may be natural or artificial.

The expression "natural variant" refers to all those variants of human CT-1 mentioned above which naturally appear in other species, that is, orthologues of CT-1. Said natural variants include, without limitation, mouse CT-1, which corresponds to the sequence with accession number Q541U3/Q60753 in the NCBI database or to the 196-amino-acid isoform that corresponds to the sequence with accession number P83714 in the NCBI database; rat CT-1, which corresponds to the sequence with accession number Q63086; macaque CT-1, which corresponds to the predicted sequence with accession number XP_001103315; dog CT-1, which corresponds to the predicted sequence with accession number XP_849072; horse CT-1, which corresponds to the predicted sequence with accession number XP_001915457; CT-1 of bovine origin, which corresponds to the predicted sequence with accession number XP_592709; and chimpanzee CT-1, which corresponds to the predicted sequence with accession number XP_592709. The natural variants of CT-1 suitable to be used in the present invention may also be derived from said sequences by means of insertion, substitution or deletion of one or more amino acids, and include natural alleles (such as variant A92T of human CT-1), variants resulting from alternative processing, and secreted and truncated forms that appear naturally.

The CT-1 that is useful in the present invention may, therefore, have a natural sequence, when it comprises a polypeptide with the same amino acid sequence as the CT-1 derived from nature. Such natural-sequence polypeptides may be isolated from nature or produced by recombinant and/or synthetic means. Thus, the CT-1 of the invention may be a recombinant protein obtained by the expression of a polynucleotide that encodes CT-1 or a functionally equivalent variant thereof in a heterologous organism, such as a bacterium, yeast or insect or mammalian cell. Said recombinant protein may be obtained as a fusion protein with an amino-terminal histidine tail that facilitates the subsequent purification thereof. The expression and purification of said proteins may be performed in accordance with methods known to those skilled in the art and described in the state of the art.

In a preferred embodiment. CT-1 is of human origin and corresponds to sequence SEQ ID NO: 1. In another preferred embodiment, CT-1 is of rat origin, preferably a fusion protein with an amino-terminal histidine tail, more preferably SEQ ID NO: 2.

In a preferred embodiment of the invention, cardiotrophin-1 is found in a concentration ranging between 0.001 mg/l and 5.000 mg/l; preferably, between 0.005 mg/l and

```
                                                            SEQ ID NO: 2
MRGSHHHHHH  GMASMTGGQQ  MGRDLYDDDD  KDRWGSMSQR  EGSLEDHQTD  SSFSFLPHLE      60

AKIRQTHNLA  RLLTKYADQL  LEEAYVQQQE  PFGLPGFSPP  RLPLAGLSGP  APSHAGLPVS     120

ERLRQDAAAL  SALPALLDAV  RRRQAELNPR  APRLLRSLED  AARQVRALGA  AVETVLAALG     160

AAARGPVPEP  VATSALFTSN  SAAGVFSAKV  LGLHVCGLYG  EWVSRTEGDL  GQLVPGGVA      239
```

Alternatively, CT-1 may be an artificial functionally equivalent variant of CT-1 which may be obtained by recombinant and/or synthetic means.

The variants of CT-1 considered in the present invention exhibit, at least, one of the functions of CT-1, such as, without limitation:
- the capacity to reduce the production of oxygen free radicals, which may be determined by methods described in the state of the art, such as that shown in the section on Materials and methods of the present invention.
- the capacity to prevent the activation of pro-inflammatory signalling pathways (NFκB), which may be determined by Western blot, as shown in the section on Materials and methods of the present invention.
- the capacity to reduce the production of inflammatory cytokines (TNFα, iNOS, IL-6), which may be determined by the methods described in the section on Materials and methods of the present invention.
- the capacity to reduce the production of pro-inflammatory adhesion molecules (VCAM-1, ICAM-1), which may be determined by Western Blot, as described in the section on Materials and methods of the present invention.
- the capacity to reduce the tissue damage and consequently to protect the renal function determined by the levels of serum creatinine (which do not increase) and by the creatinine clearance (which do not decrease). A suitable method to determine these parameters is described in the section on Materials and methods of the present invention.

Moreover, functionally equivalent variants of CT-1 considered within the context of the present invention include polypeptides that show at least 60%, 65%, 70%, 72%, 74%, 76%, 78%, 80%, 90%, 95%, 97%, 99% similarity or identity with the different natural variants of CT-1 mentioned above.

The degree of identity between two polypeptides is determined by using computer-implemented algorithms and methods that are widely known to those skilled in the art. The identity between two amino acid sequences is preferably determined using the BLASTP algorithm (BLAST Manual, Altschul, S. et al., NCBI NLM NIH Bethesda, Md. 20894, Altschul, S., et al., J., 1990, Mol. Biol. 215: 403-410).

The cardiotrophin-1 of the composition in accordance with the invention is found in a pharmacologically effective concentration. "Pharmacologically effective concentration" is understood to mean that concentration capable of producing one or more of the effects listed above which are attributable to CT-1, and may be determined by standard techniques based on the methods explained in this description.

In a preferred embodiment of the invention, cardiotrophin-1 is found in a concentration ranging between 0.001 g/l and 5.000 g/l; preferably, between 0.005 g/l and 1.000 g/l; more preferably, between 0.010 g/l and 0.500 g/l; even more preferably, between 0.08 g/l and 0.20 g/l; and even more preferably between 0.1 g/L and 0.2 g/L.

1.000 mg/l; more preferably, between 0.010 mg/l and 0.500 mg/l; even more preferably, between 0.08 mg/l and 0.20 mg/l; and even more preferably between 0.1 mg/L and 0.2 mg/L.

In the present invention, the expression "cold organ preservation solution" or "cold organ conservation solution" refers to a solution that is adequate to conserve, preserve and store organs for transplantation under hypothermic conditions, which contains substances that minimise the damages produced in the organs both during the cold ischaemia process, whilst they wait to be transplanted to the recipient subject, and in the re-perfusion process during the transplantation. Said solutions achieve the effect of conserving and preserving the organ by producing a suppression of metabolism and preventing and minimising the alterations that cold ischaemia itself may cause.

These cold organ preservation solutions exhibit their protective properties under hypothermic conditions. "Hypothermic conditions" are understood to mean temperatures below the physiological temperature, ranging between 0° C. and 25° C. In an embodiment of the invention, the cold organ preservation solution and the cold organ preservation composition of the invention are at a temperature ranging between 0° C. and 25° C.; preferably, between 0° C. and 15° C.; more preferably, between 2° C. and 7° C.; even more preferably, at approximately 4° C.

In the present invention, "cold ischaemia" is understood to mean the tissue damages and the inflammatory response caused in the organ due to its preservation under cold conditions, that is, due to the hypothermic conditions whereto it is subjected.

Within the context of the present invention, the term "re-perfusion" refers to the re-establishment of blood flow in the organ following a period of cold ischaemia.

In the present invention, "suppression of metabolism" is understood to mean the action of stopping or reducing the organ's metabolic activity and function to a minimum.

The cold organ preservation solution and, by extension, the compositions of the invention, make it possible to preserve solid organs of any species, such as, without limitation, mammals (primates, cows, horses, pigs, sheep, goats, dogs, cats, rodents, rabbits, etc.), birds, but are preferably of human origin, such as the heart, lung, pancreas, small intestine, colon, kidney. Such organs may come from a live donour or from a corpse. Within the context of the invention, the cold organ preservation solution and, by extension, the composition of the invention is especially suitable for the cold preservation of kidneys for transplantation.

Typically, the cold organ preservation solution comprises:
(a) at least one buffer agent,
(b) at least one impermeating or impermeabilising agent; and
(c) at least one electrolyte In a preferred embodiment, the cold organ preservation solution has a pH ranging between 6.5 and 8.5, and an osmolarity ranging between 300 and 410 mOsm/l, both parameters being measured at 20° C.

Within the context of the present invention, "buffer agent" is understood to mean an agent capable of controlling the pH of the solution, thereby preventing a severe acidosis that may contribute to ischaemic damage to the organ. Suitable buffer agents for the present invention are phosphate (monoacidic and diacidic), bicarbonate, sulfate, histidine, histidine-HCl. HEPES, citrate and a combination thereof. In a particular embodiment, the cold organ preservation solution comprises a buffer agent selected from the group formed by phosphate, bicarbonate, sulfate, histidine, histidine-HCl. HEPES, citrate and a combination thereof. In a preferred embodiment of the invention, the preservation solution comprises, as the buffer agent, a monoacidic phosphate and/or a diacidic phosphate and/or histidine-HCl.

The terms "impermeating agent" and "impermeabilising agent" are used interchangeably in the present invention, and refer to those agents with an osmotic capacity and which are relatively impermeable to the cell membranes, being capable of maintaining the extracellular tonicity by preventing the entry of water inside the cells, such that they prevent and/or reduce cellular swelling. Suitable impermeating or impermeabilising agents for the present invention are histidine, glucose, sucrose, mannitol, trehalose, gluconate, citrate, lactobionate, raffinose and a combination thereof, such as, for example, a combination of lactobionate and raffinose; of lactobionate and mannitol; of trehalose and gluconate; of gluconate and glucose; of gluconate and raffinose; of mannitol and citrate; of mannitol and histidine; of lactobionate, mannitol and histidine. In a particular embodiment of the invention, the cold organ preservation solution comprises an impermeating or impermeabilising agent selected from the group formed by histidine, glucose, sucrose, mannitol, trehalose, gluconate, citrate, lactobionate, raffinose and a combination thereof; preferably, selected from lactobionate, raffinose, mannitol and a combination thereof; more preferably, it comprises lactobionate and mannitol; even more preferably, it comprises lactobionate and raffinose; most preferably, it comprises lactobionate.

In a more preferred embodiment, the cold organ preservation solution comprises an impermeating agent that is selected from the group formed by lactobionate, raffinose and combinations of both.

"Electrolyte" is understood to be any substance that contains free ions, generally ions in solution, which behave as an electric conductor medium. Suitable electrolytes to be used in the present invention are sodium, potassium, magnesium, calcium, chloride and a combination thereof. In a particular embodiment of the invention, the cold organ preservation solution comprises an electrolyte selected from the group formed by sodium, potassium, magnesium, calcium, chloride and a combination thereof.

In another preferred embodiment of the invention, the cold organ preservation solution comprises glucose as the impermeating or impermeabilising agent, and, preferably, it is the Euro-Collins solution (EC). The expression "Euro-Collins solution", as used in the present invention, refers to an intracellular cold organ preservation solution that comprises high concentrations of glucose and potassium, and a low concentration of sodium. The Euro-Collins solution was originally described by G M. Collins in 1969 (Collins G M et al., 1969, Lancet, 2: 1219) and modified, by eliminating the magnesium, by the Eurotransplant Foundation in 1976 (Annual Report Eurotransplant International Foundation. Leiden, The Netherlands: Eurotransplant International Foundation, 1976), and contains glucose as the impermeating agent; chlorine, potassium and sodium as the electrolytes; and $K_2HPO_4$, $KH_2PO_4$ and $NaHCO_3$ as the buffer agents. The typical composition of the Euro-Collins solution may be the following: 195 mM glucose, 15 mM $K_2HPO_4$, 43 mM $KH_2PO_4$, 10 mM $NaHCO_3$, 15 mM chloride, 115 mM potassium and 10 mM sodium. However, said composition may vary; therefore, within the context of the present invention, a Euro-collins solution will be considered to be any solution catalogued as such in the literature or commercially available under that name.

In a particular embodiment of the invention, the cold organ preservation solution is a solution where component (a) is selected from the group formed by phosphate, bicarbonate, sulfate, histidine, histidine-HCl. HEPES, citrate and a combination thereof; component (b) is selected from the group formed by histidine, glucose, sucrose, mannitol, trehalose, gluconate, citrate, lactobionate, raffinose and a combination thereof; and/or component (c) is selected from the group formed by sodium, potassium, magnesium, calcium, chloride and a combination thereof.

The parameters that characterise the cold organ preservation solution of the invention are the pH and the osmolarity.

The term "pH" refers to the measure of acidity or alkalinity of a solution. The pH typically ranges from 0 to 14 in aqueous solution, those solutions with a pH below 7 being acidic and those with pH above 7 being alkaline. pH=7 indicates neutrality of the solution, where the solvent is water. The pH of a solution may be precisely determined by means of a potentiometer (or pH meter) and approximately determined by means of indicators, using methods that are widely known in the state of the art. Since the pH value may vary with temperature, within the context of this invention, the pH is measured at 20° C. The cold preservation solutions of the invention have a pH, measured at 20° C., ranging between 6.5 and 8.5; preferably ranging between 7.0 and 7.5.

Within the context of the present invention, the term "osmolarity" is a measure of the total concentration of substances in solution, defined as the number of osmoles of solute per litre of solution, which indicates the potential variation of the osmotic pressure that will take place in the cells upon introducing the solution into the body. The osmolarity may be calculated from the osmolality value, the latter being measured by an osmometer using methods known to those skilled in the art. Since the osmolarity is dependent on the temperature, within the context of the present invention, the osmolarity is calculated at 20° C. The osmolarity of the cold organ preservation solution of the invention, measured at 20° C., ranges between 300 and 410 mOsm/l; preferably, between 310 and 390 mOsm/l; more preferably, between 320 and 360 mOsm/l.

The cold organ preservation solution may additionally contain other components. In a particular embodiment of the invention, the cold organ preservation solution additionally comprises at least one colloid agent, at least one metabolic agent, at least one amino acid, at least one antioxidant agent, at least one vitamin and/or at least one antibiotic.

"Colloid agents" are understood to be those substances formed by numerous small particles suspended in a liquid, but which do not dissolve therein, and which are incapable of crossing semi-permeable membranes; for this reason, they are useful to prevent the expansion of the interstitial space during re-perfusion. The following, amongst others, may be incorporated as colloid agents: hydroxyethyl starch (also known as pentafraction or HES), polyethylene glycols, dextran and albumin. In a preferred embodiment of the invention, the colloid agent is HES. In another preferred embodiment of the invention, the colloid agent is polyethylene glycol. In another, even more preferred embodiment, the colloid agent is selected from the group formed by hydroxyethyl starch (HES), polyethylene glycol or a combination of both.

Within the context of the present invention, "metabolic agent" or "metabolic substrate" is understood to mean an energy precursor agent. "Amino acid" is understood to mean an organic molecule with an amino group and a carboxyl group. Metabolic agents and amino acids suitable to be incorporated into the solutions of the invention include, amongst others, adenosine, glutamate or glutamic acid, glucose, ketoglutarate, insulin, pyruvate, aspartate and tryptophan.

"Antioxidant agent" is understood to mean a sequestrant of oxygen reactive species capable of delaying or preventing the oxidation of other molecules. Antioxidant agents may include, amongst others, allopurinol, glutathione, mannitol, trolox, vitamin E, tryptophan, alpha-tocopherol and/or ascorbic acid.

The term "vitamin" refers to a substance that is not synthesised by the body and is a precursor of co-enzymes, and which participates as a catalyst in biochemical reactions. Examples of vitamins that may be used in the present invention are, without limitation, ascorbic acid, biotin, calcium-pantothenate, choline chloride, inositol, ergocalciferol, folic acid, menadione, nicotinamide, nicotinic acid, pyridoxal, riboflavin, thiamine, vitamin A, vitamin B12 and vitamin E.

"Antibiotic" is understood to mean a chemical substance produced by a living being or a synthetic derivative thereof, which, at low concentrations, kills or prevents the growth of certain classes of sensitive microorganisms. Examples of antibiotics useful in the present invention are, without limitation, trimethoprime-sulfamethoxazole, penicillin, etc.

The cold organ preservation composition of the invention may additionally contain other pharmaceutically acceptable components, that is, components approved by a regulatory agency of the federal or state governments or included in the US Pharmacopeia, or another generally recognised pharmacopeia, to be used in animals and, more particularly, in humans. These pharmaceutically acceptable components include, without limitation, diluents, coadjuvants, excipients or vehicles for the administration of the composition. Anticoagulation agents, such as heparin, may also be included. In a preferred embodiment of the invention, the composition additionally contains sodium heparin.

As those skilled in the art will appreciate, it is possible to obtain multiple combinations of these groups of components, leading to multiple embodiments of the cold organ preservation solution, all of them suitable for cold organ preservation for transplantation, and especially suitable for the preservation of kidneys for transplantation.

The cold organ preservation solutions may be extemporaneously obtained by the addition of the desired components, but they may also be cold organ preservation solutions known in the state of the art, some of which are commercially available. The cold organ preservation solutions known in the state of the art which may be used include, without limitation, the University of Wisconsin solution (UW) (Belzer FO and Southard JH. Transplantation, 1988; 45: 673), the Institut Georges Lopez solution (IGL-1) (Ben Abdennebi H et al. Transpl Int 2002; 15: 348), the Celsior solution (CEL) (Menasche P et al. Eur J Cardiothorac Surg, 1994; 8: 207), the Kyoto solution (ET-Kyoto) (Chen F at al. Yonsei Med J, 2004; 45: 1107-1114), the Polysol solution (Wei L et al. World J Gastroenterol, 2007; 13: 3684-3691), the Bretschneider or histidine-tryptophan-ketoglutarate solution (HTK) (Bretschneider HJ. Thorac Cardiovasc Surg, 1980; 28: 295), Marshall's solution (HOC or hyperosmolar citrate) (Southard JH, Belzer FO. Annu Rev Med 1995; 46: 235), the Euro-Collins solution (EC) (Annual Report Eurotransplant International Foundation. Leiden, The Netherlands: Eurotransplant International Foundation, 1976), sucrose phosphate buffer (Lam FT et al. Transplantation, 1989; 47: 767), the PERFADEX™ solution (Müller C at al. Transplantation, 1999; 68: 1139-43), St. Thomas Hospital solutions 1 and 2 (STH-1, STH-2) (Michel P et al. J Heart Lung Transplant, 2002; 21: 1030-9), the Lyon preservation solution (LYPS) (Michel P at al. J Heart Lung Transplant, 2000; 19: 1089-1097) or the Stanford solution (STF) (Michel P at al. J Heart Lung Transplant, 2002; 21: 1030-9).

Alternatively, cold organ preservation solutions may be used which are suitable for hypothermic perfusion machines, such as the above-mentioned solutions or modifications thereof, for example, the modified UW-gluconate solution (Belzer MPS).

Thus, in a preferred embodiment of the invention, the cold organ preservation solution comprises lactobionate and HES. In another embodiment, the cold preservation solution of the invention comprises lactobionate and a polyethylene glycol. In yet another embodiment of the invention, the cold preservation solution comprises lactobionate, raffinose and HES, and, in particular, said solution is the University of Wisconsin solution (UW). The expression "University of Wisconsin solution (UW)", as used in the present invention, refers to a cold organ preservation solution that comprises HES as the colloid agent, and lactobionate and raffinose as the impermeating agents. Typically, the University of Wisconsin solution additionally contains at least one buffer agent, such as $KH_2PO_4$, and at least one electrolyte, such as chloride, magnesium sulfate, potassium and sodium. Moreover, the typical composition of said solution includes antioxidant agents such as allopurinol and glutathione, and additives such as adenosine. Specifically, the University of Wisconsin solution developed by Belzer and Southard (Transplantation, 1988; 45: 673) comprises HES (50 g/l) as the colloid agent, lactobionate (100 mM) and raffinose (30 mM) as the impermeating agents, $KH_2PO_4$ (25 mM) as the buffer agent, chloride (20 mM), magnesium sulfate (5 mM), potassium (120 mM) and sodium (25 mM) as the electrolytes, allopurinol (1 mM) and glutathione (3 mM) as the antioxidant agents, and adenosine (5 mM) as the additive. However, the composition of said solution may vary, and it is found in both the documents of the state of the an (U.S. Pat. No. 4,879,283) and in commercial solutions. UW solutions that lack some non-essential component, such as the chloride ion, or those the components whereof have slightly variable concentrations. Therefore, the University of Wisconsin solution useful in the present invention includes all those solutions that are commercialised as Wisconsin solution or those catalogued in the literature as such, regardless of whether or not the composition matches that described by Belzer and Southard.

In another embodiment of the invention, the cold preservation solution of the invention comprises lactobionate, raffinose and a polyethylene glycol, and, in particular, said solution is the Institut Georges Lopez solution (IGL-1).

In another embodiment of the invention, the cold preservation solution comprises lactobionate, raffinose and mannitol, and, in particular, said solution is the Celsior solution.

In another embodiment of the invention, the cold preservation solution comprises gluconate, trehalose and HES, and, in particular, said solution is the Kyoto solution (ET-Kyoto).

In another embodiment of the invention, the cold preservation solution comprises gluconate, trehalose and a polyethylene glycol, and, in particular, said solution is the Polysol solution.

In another embodiment of the invention, the cold preservation solution comprises histidine and mannitol, and, in particular, said solution is the Bretschneider solution (HTK, histidine-tryptophan-ketoglutarate).

In another embodiment of the invention, the cold preservation solution comprises citrate and mannitol, and, in particular, it is Marshall's solution (HOC or hyperosmolar citrate).

Those skilled in the art will appreciate that the compositions of the invention may be formed by a single composition wherein cardiotrophin-1 (CT-1) or the functionally equivalent variant thereof is dispersed in the cold organ preservation solution. However, the invention considers that both components are separate in the form of a "kit-of-parts", such that the final composition may be prepared at the suitable time, for example, just prior to being used, by combining both components.

The term "kit", as used in this document, refers to a combination of a set of components suitable to obtain the compositions in accordance with the invention, jointly with the appropriate containers and packages used for commercial sale, etc.

In the present invention, "component suitable to obtain the compositions in accordance with the invention" refers to any compound that may be used to obtain (i) and (ii), and includes, without limitation, media, additives. CT-1, electrolytes, impermeabilising agents, buffers, cold organ preservation solutions, etc.

Thus, for example, the kit may comprise:

i) a container with the completely constituted cold organ preservation composition, wherein cardiotrophin-1 (or the functionally equivalent variant thereof) is already mixed with the cold organ preservation solution;

ii) alternatively, a container with the constituted or partially constituted cold organ preservation solution; an additional container that comprises cardiotrophin-1 (or a functionally equivalent variant thereof); and, optionally, other containers with constituents of the cold organ preservation solution or additional additives, wherein mixing of the components to prepare the completely constituted cold organ preservation composition of the invention is performed just prior to being used;

iii) alternatively, various containers with the necessary media and constituents for the preparation of the cold organ preservation composition of the invention, where at least one of said containers will contain cardiotrophin-1 (or a functionally equivalent variant thereof).

The media, constituents and additives for the preparation of the cold organ preservation composition in accordance with the invention must be pharmaceutically acceptable. The term "pharmaceutically acceptable" means approved by a regulatory agency of the Federal or a state government, or included in the US or another generally recognised pharmacopeia, to be used in animals and, more particularly, in humans. Media and additives are understood to be diluents, coadjuvants, excipients or vehicles wherewith the composition of the invention is administered. Such media and additives may be sterile liquids.

Thus, one aspect of the invention relates to a kit for the preparation of a cold organ preservation composition that comprises:

(i) cardiotrophin-1 or a functionally equivalent variant thereof; and (ii) a cold organ preservation solution or, alternatively, media and additives for the preparation of said solution.

The different embodiments of the kit of the invention as regards the cold organ preservation compositions obtained by means of said kit have been previously described within the context of the compositions of the invention.

Methods of Preparing the Composition of the Invention

Another aspect of the invention relates to a method of preparing a cold organ preservation composition that comprises adding cardiotrophin-1 or a functionally equivalent variant thereof to a cold organ preservation solution.

The expressions "cold organ preservation composition", "cardiotrophin-1", "functionally equivalent variant" and "cold organ preservation solution", as well as the components thereof and the parameters that characterise them, have been previously defined and described in detail within the context of the compositions of the invention.

In a preferred embodiment, the cold organ preservation solution comprises (a) at least one buffer agent (b) at least one impermeating or impermeabilising agent; and (c) at least one electrolyte.

In an even more preferred embodiment, the cold organ preservation solution has a pH ranging between 6.5 and 8.5; and an osmolarity ranging between 300 and 410 mOsm/l, both parameters being measured at 20° C.

The preparation of said cold organ preservation composition may be performed extemporaneously, just prior to being used, by adding a therapeutically effective quantity of cardiotrophin-1 or a functionally equivalent variant thereof to a cold organ preservation solution. Said cold organ preservation solution may be a commercial solution, a solution known in the state of the art, or a solution obtained by mixing at least one buffer agent, at least one impermeating or impermeabilising agent, and at least one electrolyte, in order to obtain a solution with a pH ranging between 6.5 and 8.5; and an osmolarity ranging between 300 and 410 mOsm/l, both parameters being measured at 20° C. The composition in accordance with the invention may also be previously prepared and preserved under cold conditions until it is to be used.

In preferred embodiments of the invention, the cold organ preservation composition prepared by this method may be any composition included amongst those described within the context of the first aspect of the invention.

In a preferred embodiment, the method of preparing the composition of the invention is performed using cardiotrophin-1 of human origin, more particularly, the cardiotrophin-1 that corresponds to SEQ ID NO: 1. In a preferred embodiment, the method is performed such that the final concentration of cardiotrophin-1 in the composition ranges between 0.001 g/L and 5.000 g/L; preferably, between 0.005 g/L and 1.000 g/L; more preferably, between 0.010 g/L and 0.500 g/L; even more preferably, between 0.08 g/L and 0.20 g/L; and even more preferably, between 0.1 g/L and 0.2 g/L. In an even more preferred embodiment, the method is performed such that the final concentration of cardiotrophin-1 in the composition ranges between 0.001 mg/L and 5.000 mg/L; preferably, between 0.005 mg/L and 1.000 mg/L; more preferably, between 0.010 mg/L and 0.500 mg/L; even more preferably, between 0.08 mg/L and 020 mg/L; and even more preferably, between 0.1 mg/L and 0.2 mg/L.

Cold Preservation Methods of the Invention

Another aspect of the invention relates to a method for the cold preservation of an organ, which comprises contacting said organ with a cold organ preservation composition that comprises (i) cardiotrophin-1 (CT-1) or a functionally equivalent variant thereof; and (ii) a cold organ preservation solution.

The expression "cold organ preservation solution" has been explained in detail in relation to the compositions of the invention. In a preferred embodiment, the cold organ preservation solution comprises (a) at least one buffer agent (b) at least one impermeating or impermeabilising agent; and (c) at least one electrolyte.

In a preferred embodiment, the cold organ preservation solution has a pH ranging between 6.5 and 8.5; and/or an osmolarity ranging between 300 and 410 mOsm/l, both parameters being measured at 20° C.

"Cold preservation of an organ" is understood to mean the capacity to conserve, preserve, protect and/or store an organ, under hypothermic conditions, minimising the cell damage thereto by a suppression of metabolism and by preventing or counteracting the alterations caused in the organ by both cold ischaemia and re-perfusion of said organ. Said cold preservation of an organ can be performed on the human or animal body wherefrom it is obtained, outside said body or both on the body and outside it.

In a preferred embodiment of the invention, the organ is isolated. By "isolated" is understood to mean an organ which has been extracted from the donor and which is outside the human or animal body wherefrom it is obtained, "Contacting an organ" with a cold organ preservation composition in accordance with the invention is understood to mean that said composition is made to come in contact with said organ, by means of washing, immersion or perfusion.

The cold organ preservation methods, especially those aimed at organs for transplantation, generally comprise a first stage wherein said organ is perfused with a cold organ preservation liquid. Within the context of the present invention, "perfusion" is understood to mean intravascular washing of the organ through a cannula introduced therein, in order to eliminate blood residues from the donour that might hinder the subsequent preservation steps, and also in order to replace said blood with the cold preservation liquid, such that the organ is cooled to the desired temperature.

Said perfusion can be performed on the organism of a live or dead donor or on the isolated organ. The inventors have demonstrated that the perfusion of the organ with a composition according to the invention is enough to suitably store it and/or preserve it without the need for subsequent treatments with the same composition. Therefore, in a particular embodiment of the invention the composition is contacting with the organ by means of in vivo perfusion in the donor. In a still more particular embodiment, the organ perfused in vivo with said composition is not maintained after the extraction immersed in a composition according to the invention.

In the context of this invention, in "vivo perfusion" is understood as the perfusion carried out on the body of a live human or animal donor.

In another embodiment of the invention, the composition is contacting with the organ by means of perfusion when said organ is isolated from the donor. In a still more particular embodiment, the isolated organ perfused with said composition is not maintained after the extraction immersed in a composition according to the invention. In another particular embodiment, the isolated organ perfused with said composition is maintained immersed in a composition according to the invention.

Perfusing in the isolated organ is understood as taking place once it has been extracted from the donor. In a particular embodiment, the organ may have been perfused "in vivo" by a "cold organ preservation solution", to then be perfused again with the composition according to the invention once isolated. Subsequently, it is not maintained immersed in the composition according to the invention.

In another embodiment of the invention, the composition is contacting with the organ by means of perfusion in the donor and by means of immersion after the extraction.

The present invention also contemplates physical interventions on a human or animal organism in which the maintenance of the life and the health of said organism are not of great importance. Therefore, in another particular embodiment of the invention the organ comes from a dead donor. In a still more particular embodiment, the composition is contacting with the organ by means of perfusion in the dead donor. In an even more particular embodiment, the organ perfused with said composition is not maintained after he extraction immersed in a composition according to the invention.

In another embodiment, the composition is contacting with the isolated organ extracted from the dead donor by means of perfusion and after said perfusion, by means of immersion. In another embodiment, the composition is contacted with the isolated organ extracted from the dead donor by means of perfusion and after said perfusion, it is not maintained immersed in a composition according to the invention.

In the context of this invention, "dead" is understood as a human or animal body in which vital activity of the entire brain, including the brain stem, has irreversibly ceased and been verified by means of well-defined neurological clinical protocols and is supported by specialized tests known by a person skilled in the art. In the present document, the term "dead" includes, in addition to cadavers, organisms in a state of cerebral death or brain death whose heart and breathing activity are artificially maintained.

In the context of this invention, the term "donor" relates to human or animal organisms from which the organ for transplantation originates.

Following perfusion, the organ may be washed and/or subjected to immersion. Within the context of the present invention, "washing" is understood to mean treatment of the outer and/or inner surface of the organ with a cold organ preservation composition or solution for a short period of time.

In general, between extraction of the organ from the donour and transplantation to the recipient, a period of hours or even days may elapse. In these cases, the extracted organ is preserved by immersion in a cold organ preservation composition or solution. Within the context of the present invention, "immersion" is understood to mean submerging the organ in the preservation solution. The organ may be submerged, for example, in a container with the composition of the invention in a sufficient quantity to cover said organ.

Alternatively, the organ may be preserved in storage in hypothermic perfusion machines. Such machines are devices that maintain a controlled, continuous or pulsating, flow with a cold organ preservation composition in accordance with the invention.

Finally, the composition of the invention may also be perfused during the re-perfusion period, that is, when the organ that has undergone cold ischaemia recovers the blood flow.

In each case, the necessary quantity of cold preservation liquid will be used.

The organ may remain in contact with the composition of the invention for a period of time that ranges from seconds to hours or days. Typically, the organ and the composition are kept in contact outside the body for at least 150 seconds, at least 30 minutes, at least 3 hours, at least 6 hours, at least 12 hours, at least 24 hours, at least 48 hours, at least 72 hours, etc.; preferably, between 24 and 48 hours; more preferably, 24 hours. During the entire contact time between the composition in accordance with the invention and the organ, the ensemble must be maintained at a temperature ranging between 0° C. and 25° C.; preferably, between 0° C. and 15° C.; more preferably; between 2° C. and 7° C.; and even more preferably, at approximately 4° C.

For example, perfusion of a human kidney may be performed for 10-15 minutes using a volume of cold preservation liquid of up to 10 times the weight of the kidney. Subsequently, this kidney may be stored in a cold preservation solution for a period that may range between several seconds and 72 hours, depending on the needs.

Within the context of the present invention, the organ may be alternatively subjected to perfusion, immersion or washing in the composition in accordance with the invention; or to a combination thereof. In an embodiment of the invention, a first perfusion of the organ is performed with the cold preservation composition of the invention and, subsequently, the organ is stored and preserved in said solution until the time of transplantation. The first stage of perfusion can be performed on the organ of a live donor or a dead donor. Therefore, in another particular embodiment, the composition is contacting with the organ by in vivo perfusion in the donor and, after the extraction, by immersion. In another particular embodiment, the composition is contacting with the organ by perfusion on the dead donor and, after the extraction, by immersion.

The invention also considers the possibility that the perfusion is performed with a cold preservation solution lacking cardiotrophin-1 and that, subsequently, the compositions in accordance with the invention are used to maintain the organ by immersion or washing.

In a preferred embodiment of the invention, the cold organ preservation composition is contacting with the organ by washing, immersion, perfusion or a combination thereof.

In preferred embodiments, the cold organ preservation composition used in this method is a cold preservation composition as explained above within the context of the compositions of the invention.

The organ that is contacting with the method of the invention may be any solid organ from any species, such as, without limitation, mammals (primates, cows, horses, pigs, sheep, goats, dogs, cats, rodents, rabbits, etc.), birds, but it is preferably of human origin. Said organ may come from a live donour or a corpse from the same species or a species other than that of the recipient. Suitable organs for the cold preservation method of the invention may be, without limitation, the heart, lung, pancreas, small intestine, colon, kidney. In a preferred embodiment of the invention, the organ that is contacting with the composition of the invention is the kidney. In another preferred embodiment of the invention, the organ is the lung. Yet in another preferred embodiment, the organ is the heart.

Uses of the Invention

Another aspect of the invention relates to the use of cardiotrophin-1 or a functionally equivalent variant thereof for the preparation of a composition for cold organ protection and/or preservation for transplantation.

In preferred embodiments of the invention, the cold organ preservation composition is a composition as described above within the context of the compositions of the invention.

Another aspect of the invention relates to the use of a composition in accordance with the invention for cold organ protection and/or preservation for transplantation.

Another aspect of the invention relates to a composition for the cold organ preservation in accordance with the invention for use in cold organ protection and/or preservation for transplantation."Cold organ protection and/or preservation for transplantation" is understood to mean the capacity to conserve, preserve, protect and/or store an organ under hypothermic conditions, minimising the cell damage thereto by a suppression of metabolism and preventing or counteracting the alterations caused in the organ by both cold ischaemia and the re-perfusion of said organ produced at the time of transplantation.

In a particular embodiment of the invention, the cold protection and/or preservation of organs for transplantation is performed in vivo in the donor, preferably by means of in vivo perfusion. Said in vivo protection and/or preservation takes place in the human or animal body of the donor, usually by means of perfusing the composition according to the invention.

In another particular embodiment of the invention, the cold protection and/or preservation of organs for transplantation is performed in two steps: first in vivo perfusion is performed in the donor with the "cold organ preservation solution" not containing cardiotrophin, and then the organ is extracted. Once the organ is isolated, in a second step it is again perfused with the composition of the invention.

Once the organ is perfused with the composition of the invention, either in vivo or once isolated, said isolated organ can optionally be preserved and/or protected by subjecting it to immersion in said composition. Therefore, in another particular embodiment, the cold protection and/or preservation is performed by means of in vivo perfusion of the composition of the invention in the donor or in the isolated organ and after the organ for transplantation is extracted from the donor it is additionally subjected to immersion in said composition. In another particular embodiment, the cold protection and/or preservation is performed by means of perfusing the composition according to the invention in the isolated organ of the donor and additionally by means of immersing said organ in said composition.

The present invention also contemplates physical interventions on a human or animal organism in which the maintenance of the life and the health of said organism are not of great importance. Therefore in another particular embodiment of the invention, the cold protection and/or preservation of organs for transplantation is performed by means of perfusing in the human or animal body of a dead donor.

In the context of this invention, "dead" is understood as a human or animal body in which vital activity of the entire brain, including the brain stem, has irreversibly ceased and been verified by means of well-defined neurological clinical protocols and is supported by specialized tests known by a person skilled in the art. In the present document, the term "dead" includes, in addition to cadavers, organisms in a state of cerebral death or brain death whose heart and breathing activity are artificially maintained.

In a preferred embodiment of the invention, the organ for transplantation is isolated. "Isolated" is understood as an organ that has been extracted from the human or animal organism from which it derives and is outside said organism.

The organs for transplantation that are used in the method of the invention may be any solid organ of any species, such as, without limitation, mammals (primates, cows, horses, pigs, sheep, goats, dogs, cats, rodents, rabbits, etc.), birds, but they are preferably of human origin. Said organ may come from a live donour or a corpse from the same species or a species other than that of the recipient. Suitable organs for the cold preservation method of the invention may be, without limitation, the heart, lung, pancreas, small intestine, colon, kidney. In a preferred embodiment of the invention, the organ that is protected and/or preserved for transplantation with the composition of the invention is the kidney. In another preferred embodiment of the invention, the organ that is protected and/or preserved for transplantation with the composition of the invention is the lung. Yet in another preferred embodiment, the organ is the heart.

Preserved Organs of the Invention

The authors of the present invention have demonstrated that the compositions of the invention make it possible to reduce the damages associated with cold ischaemia and post-transplantation re-perfusion in said organs. Moreover, the authors of the present invention have shown that the compositions of the invention are suitable for the cold preservation of kidneys for transplantation, since they prevent the tubular necrosis caused by ischaemia-re-perfusion, thereby improving the renal function (reduction of the levels of serum creatinine and increase in creatinine clearance) and the survival rate (FIG. 4).

Therefore, another aspect of the invention relates to a cold-preserved isolated organ obtained by means of the methods in accordance with the present invention.

The term "organ", as used herein, refers to a differentiated part of the body, which has a specific function. Examples include, without being limited thereto, parts that have specific functions such as breathing, secretion or digestion. Said organs are "isolated", that is, outside the animal or human body wherefrom they derive. Isolated organs preserved in accordance with the present invention include, without limitation, the heart, kidney, lung, heart, heart-lung, intestine, spleen and thymus.

In a preferred embodiment, the preserved isolated organ is a kidney. In another preferred embodiment, the preserved isolated organ is a lung. Yet in another preferred embodiment, the preserved isolated organ is a heart.

The preserved organs are particularly useful in therapies based on transplantations.

The invention is described below by means of the following examples, which must be considered to be merely illustrative, and in no case considered to limit the scope of the present invention.

EXAMPLES

Materials and Methods
Preparation and Analysis of the Samples

A portion of the kidney was separated and washed with homogenate buffer [0.05 M potassium phosphate monobasic and 1 mM EDTA, with 0.25% sodium cholate; pH 7.8], at a temperature ranging between 0° C. and 4° C., in order to minimise oxidation processes. Subsequently, it was weighed and homogenised with a quantity of the same homogenate buffer in a proportion of 1:10 w/v. The homogenate was centrifuged at 100,000 g for 60 minutes, at a temperature of 4° C. The soluble fraction obtained was divided into aliquots and frozen at −80° C. for preservation until it was to be analysed. These samples were used to determine the renal levels of superoxide anion (SOA). TNFα and IL-6.

Another portion of the kidney was separated in order to determine the proteins by Western Blot. In the first place, the sample was homogenised in lysis buffer (25 mM HEPES, pH 7.5; 150 mM NaCl; 1 mM EDTA; 1% IGEPAL CA-630; 10% Glycerol; 10 mM $MgCl_2$; 0.25% Sodium deoxycholate; 10 µg/ml aprotinin; 10 µg/ml leupeptin; 10 mM phenyl methyl sulfonyl fluoride (PMSF); 100 mM Sodium Orthovanadate $Na_2VO_4$; and 25 mM Sodium Fluoride (NaF)), in a proportion of 1 ml/100 mg of tissue and for 30-60 minutes in ice. Subsequently, it was centrifuged for 25 minutes at 12,000 g and 4° C.; the supernatant was collected and frozen in aliquots at −80° C. until it was to be used.

Determination of the Production of Superoxide Anion $O_2^-$ (SOA)

In order to determine SOA production levels in the kidney, a modification of the technique described by Boveris for mitochondria [Boveris A. *Methods Enzymol*. 1984; 105: 429-435], based on the reduction of cytochrome C by the $O_2^-$ radical, was used. Briefly:

- a spectrometry cuvette (1-ml cuvettes) was prepared by adding 100 µl of cytochrome C (75 µM), 20 µl of superoxide dismutase (SOD; approximately 264 U), 25 µl of sample and buffer solution (0.1 M potassium phosphate +0.1 mM EDTA; pH 7.8) to complete a volume of 1,000 µl;
- a reference cuvette was prepared, without added sample, by adding 100 µl of cytochrome C (75 µM), 20 µl of SOD and buffer solution until a volume of 1,000 µl was completed;
- another similar cuvette was prepared which did not contain SOD, in order to study the non-specific reduction of cytochrome C;
- the reduction of cytochrome C was followed by means of spectrophotometric readings [at a λ of 550 nm; pH 7.8 and a temperature of 25° C., for 1 minute with 6-second intervals, in 1-ml cuvettes, with a 1-cm light passage] in 2 phases, 1.—non-specific reduction of cytochrome C (without SOD), and 2.—superoxide-dependent reduction of cytochrome C (with SOD);
- the increase in absorbance units in the reaction mixture was converted into nmoles of SOA with the molar extinction coefficient: $\Delta E_{550}/21.0 \times 10^3$ $M^{-1}$ $cm^{-1}$, under the assumption that the cytochrome C in the reference cuvette is completely oxidised and that the increase in absorbance observed solely represents the absorbance of the reduced product. Δ absorbance: reduced—oxidised;
- in this way, the production of the SOA superoxide anion was expressed in nmol/mg protein/minute.

Determination of Cytokines TNFα and IL-6

The levels of TNFα in renal tissue, in serum and in the preservation liquid were determined by means of ELISA, using a DuoSet ELISA Development System rat TNFα/TNFSF1A kit (R&D Systems; Minneapolis, USA), in accordance with the manufacturer's instructions.

Likewise, the levels of IL-6 were determined by means of ELISA, using a commercial DuoSet ELISA Development System rat IL-6 kit (R&D Systems).

In both cases, the levels were expressed in pg/ml.

Determination of iNOS, sICAM-1, sVCAM-1, IκB and NFκB by Western Blot

In order to quantify the proteins by Western Blot, the tissue samples were diluted (1:20) in lysis buffer and a Bio-Rad kit, based on the Lowry method, was used. The reaction was performed in 96-well plates (Microtest™ 96, Becton Dickinson Labware, N.J., USA) using 5 µl for both the samples and the standard curve. Each measurement was performed in triplicate. Prior to this, a calibration curve was prepared on the basis of standard solutions with a known concentration of BSA. Subsequently, 25 µl of reagent A (supplemented with 20 µl of reagent S for every ml of reagent A. since the samples contained detergent: IGEPAL CA-630) were added. Thereafter, 200 µl of reagent B were 35 added. The mixture was incubated for at least 15 minutes and the absorbance was measured at 750 nm.

Separation of the proteins by electrophoresis is based on the Laemmli method. The proteins were loaded in a 1.5-mm thick Tris-glycine-polyacrylamide gel containing a 17% acrylamide mix loading gel (29.2% acrylamide, 0.8% bis-acrylamide) and an acrylamide mix separation gel with a variable thickness, depending on the size of the protein and the sample volume to be loaded. A molecular weight marker was also loaded (Low/Broad range, Bio-Rad Laboratories, CA, USA or BenchMark™ Pre-Stained Protein Ladder, Invitrogen Corporation, CA, USA).

The quantity of tissue extract used was 200 µg of protein/well. Each sample was mixed with an equal volume of loading buffer (1% 2-mercaptoethanol, 2% sodium dodecyl sulfate [SDS], 10% glycerol, 125 mM Tris, pH 6.8, 0.0005% w/v bromophenol blue); the proteins were denatured at 100° C. for 5 minutes and, subsequently, a small quantity of loading buffer was deposited in the wells without a sample, filling the remaining space of all the wells with electrophoresis buffer (192 mM glycine, 0.1% SDS, 25 mM Tris base, pH 8.3).

The electrophoresis was performed in electrophoresis buffer applying a constant voltage of 100 V.

The proteins separated and included in the acrylamide gel were transferred to a membrane. The transfer was performed in a cuvette with transfer solution (190 mM glycine, 20 mM Tris, pH 8.3), keeping a constant amperage of 400 mA, having previously soaked the material (blotting papers and sponges) and equilibrated the gel and the nitrocellulose membrane (Hybond-ECL Amersham Biosciences) in the transfer buffer for 15 minutes.

Once the transfer was concluded, the membrane was washed with TTBS washing buffer (0.1% v/v TWEEN-20; 150 mM NaCl; 20 mM Tris, pH 7.5) and, immediately thereafter, incubated with 10 ml of blocking buffer under constant stirring, in order to prevent non-specific bonds during immunodetection. Incubation with the primary antibody, at the adequate dilution and temperature in the corresponding buffer, under constant stirring, was performed for different times depending on each protein. Following incubation with the primary antibody, 4 5-minute washings were performed with washing buffer and, subsequently, the membrane was incubated with the corresponding secondary antibody, at the adequate dilution, for a specified time with each protein. At the end, 4 additional 5-minute washings were performed with washing buffer.

The specific bands of the different proteins were detected by means of a chemoluminescence assay; to this end, a mixture of commercial development solutions (Amersham Biosciences, United Kingdom), in a 1:1 proportion, was kept under constant stirring for 1 minute at ambient temperature and, subsequently, the development solution was discarded. Thereafter, the membrane was placed in a chamber in order to capture the image (ImageQuant RT ECL Imager, GE Healthcare). Once the image was captured, the optical density of the bands obtained was quantified with the programme (ImageQuant TL software).

Following each determination, a "stripping" was performed with a commercial solution (Re-Blot Plus Strong Antibody Stripping Solution, Chemicon International, CA, USA), in order to subsequently quantify α-tubulin, which was used as a loading control.

The antibodies used were:
Anti-α-Tubulin (#2144# Cell Signaling Technology)
iNOS/NOS Type II (BD Transduction Laboratories, 610332)
Anti ICAM-1 (Santa Cruz Biotechnology, INC. sc-1511)
Anti VCAM-1 (Santa Cruz Biotechnology, INC. sc-1504)
Anti IκB-β (R&D Systems, MAB3425)
Anti NFκB (Santa Cruz Biotechnology, NFκB p65 (F-6): sc-8008)
Anti pNFid3 (Santa Cruz Biotechnology, p-NFκB p65 (A-8): sc-166748)

Analysis of the Renal Function (Creatinine and Creatinine Clearance)

In order to measure the renal function, the plasma concentrations of creatinine and the creatinine clearance, which is a measure of the glomerular filtration rate, were determined. The creatinine clearance (CCr) was calculated using the formula:

$$CCr = FU \times CrO / CrP,$$

where FU is the urine flow rate (ml/min). CrO is the concentration of creatinine in the urine (mg/ml) and CrP is the plasma concentration of creatinine (mg/ml). The concentration of creatinine in the urine and in plasma was measured by means of a semi-automatic analyser (Reflotron, Roche).

Statistics

The statistical analysis of the data was performed by means of double-entry variance analysis, followed by the Schon or the Kruskal-Wallis test, depending on whether the data were parametric or non-parametric. Significant differences were considered to be those with a p-value lower than or equal to 0.005. The NCSS 2000 statistical programme (Dr. Jerry L. Hintze, Utah, USA) was used for the analysis.

Example 1

Preparation of Cold Organ Preservation Compositions

Different cold organ preservation compositions were prepared, supplemented with cardiotrophin-1 (CT-1), using the Euro-Collins solution (EC) or, alternatively, the University of Wisconsin solution (UW), as the base cold organ preservation solution.

Since the cold preservation solutions were to be assayed in experimental rat models, in order to supplement the media, rat CT-1 supplied by DRO Biosystems was used. It was produced in *E. Coli* BL21 (Invitrogen, Barcelona, Spain) as a fusion protein with an amino-terminal histidine tail. The expression of the recombinant protein was induced with IPTG (Sigma) for a final concentration of 0.5 mM in 2 hours at 25° C. After homogenising the bacteria pellet, the His-CT-1 fusion protein was purified by means of nickel affinity column chromatography (Qiagen, Barcelona, Spain). The sequence of CT-1 used is SEQ ID NO: 2:

```
MRGSHHHHHH GMASMTGGQQ MGRDLYDDDD KDRWGSMSQR EGSLEDHQTD SRFSFLPHLE     60

AKIRQTHNLA RLLTKYADQL LEEYVQQQGE PFGLPGFSPP RLPLAGLSGP APSHAGLPVS    120

ERLRQDAAAL SALPALLDAV RRRQAELNPR APRLLRSLED AARQVRALGA AVETVLAALG    180

AAARGPVPEP VATSALFTSN SAAGVFSAKV LGLHVCGLYG EWVSRTEGDL GQLVPGGVA     239
```

The EC solution was purchased from Laboratorios Esteve (Barcelona, Spain) and the UW solution was purchased from Bristol-Myers-Squibb (ViaSpan; Bristol-Myers-Squibb S.L.; Madrid; Spain).

For the organ preservation and transplantation assays, different cold organ preservation compositions were prepared by adding different quantities of CT-1 to the base solution. Tables 1 and 2 show the composition of the different cold organ preservation compositions that were prepared.

TABLE 1

Composition of the EC cold organ preservation solution and the EC[CT1] composition in accordance with the invention

|  | EC | EC[CT1] |
|---|---|---|
| CT-1 | (0.0 mg/l) | (0.1 mg/l) |
| Monohydrate glucose |  | 200 (38.64 g/l) |
| $K_2HPO_4$ |  | 15 (1.6 g/l) |
| $KH_2PO_4$ |  | 43 (8.3 g/l) |
| KCl |  | 15 (0.1088 g/l) |
| $NaHCO_3$ |  | 10 |
| Content of: |  |  |
| Chloride |  | 15 |
| Potassium |  | 115 |
| Phosphates |  | 57 |
| Sodium |  | 10 |
| pH at 20° C. |  | 7.4 |
| Osmolality |  | 370 mOsm/kg |

Except as otherwise specified, the concentrations are given in mmol/l, and the equivalence in g/l is given in parentheses.
This composition was used for the kidney cold preservation assays with EC[CT1] (Example 2, FIG. 1).

TABLE 2

Composition of the UW cold organ preservation solution and the UW[CT1] composition in accordance with the invention

|  | UW | UW[CT1] |
|---|---|---|
| CT-1 | (0.0 mg/l) | (0.1 mg/l)[a] |
|  |  | (0.2 mg/l)[b] |
| Poly(0-2-hydroxyethyl) starch 0.40-0.50 $MS^1$) (Pentafraction) |  | (50 g/l) |
| Lactobionic Acid (as lactone) |  | 105 (35.83 g/l) |
| Raffinose × 5 $H_2O$ |  | 30 (17.83 g/l) |
| Allopurinol |  | 1 (0.136 g/l) |
| Reduced Glutathione |  | 3 (0.922 g/l) |
| Adenosine |  | 5 (1.34 g/l) |
| $KH_2PO_4$ |  | 25 (3.4 g/l) |
| 40%NaOH |  | 27 (3.679 g/l) |
| 56% KOH |  | 100 (14.5 g/l) |
| $MgSO_4 × 7 H_2O$ |  | 5 (1.23 g/l) |
| pH at 20° C. |  | 7.4 |
| Osmolality |  | 320 mOsm/kg |

Except as otherwise specified, the concentrations are given in mmol/l, and the equivalence in g/l is given in parentheses.
[1]MS = moles of hydroxyethyl per moles of anhydroglucose units
[a]For the kidney cold preservation assays with UW[CT1] (Example 2 and FIG. 2) and the cold preservation assays with UW[CT1] and kidney transplantation (Example 4 and FIG. 4), the cold organ preservation composition contained 0.1 mg/l of CT-1.
[b]For the kidney cold preservation assays with UW[CT1] (Example 3 and FIG. 3), the lung, heart and heart-lung cold preservation assays (Example 5 and FIGS. 5, 6 and 7) and the renal cold preservation study with UW[CT1] used only in the perfusion liquid, only in the preservation liquid or in both (Example 6, FIG. 8), the cold organ preservation composition contained 0.2 mg/l of CT-1.

Example 2

Studies of Cold Renal Preservation With a Cardiotrophin-1 Concentration of 0.1 mg/l Wistar rats were used (225-300 g/rat males for the first study, and 225-250 g/rat males for the second study). The rats were anaesthesised by intraperitoneal injection with ketamine chloride (75 mg/kg)+diazepam (50 mg/kg) and atropine (20 mg/kg). A median laparotomy was performed and the retroperitoneum was dissected in order to expose the abdominal aorta and the renal arteries to the aortic bifurcation (iliac arteries). Subsequently, the renal vessels were dissected by means of ligation of the inferior and gonadal suprarrenal branches; and the ureter was dessicated at the proximal half, respecting the periurethral fat.

Subsequently, for perfusion of the organ (washing perfusion), the aorta was clamped below the renal artery exit, thereby maintaining the vascularisation thereof. The aortic catheterisation was performed by means of transverse aortotomy on the front face, following distal ligation at the bifurcation. The aorta was occluded by means of ligation above the left renal artery, whilst the clamp was removed in order to initiate the cold perfusion (4° C.) with the cold organ preservation composition to be assayed and with 1 mg/kg of sodium heparin. The drainage was performed through the renal vein, which was sectioned at the joint with the vena cava.

Once the kidney was perfused, the ureter (in the dessicated path) and the renal artery were sectioned. The kidney was extracted and submerged in a container with the cold preservation composition to be assayed, in a sufficient quantity to cover the organ, and kept at a temperature of 4° C.

Following cold preservation for a pre-set time, samples were collected in order to analyse the different target parameters.

In each study, parallel assays were performed, with different groups of animals, in order to evaluate and compare the preservation efficacy of: i) different cold preservation compositions; and ii) different pre-set preservation times (3 hours, 6 hours, 12 hours, 24 hours and 48 hours, respectively).

In each study, a "simulated" group of rats (Sim) was also included, in order to determine the baseline values of the parameters studied without preservation (time 0 of preservation). The simulated group consisted of extracting the kidney, subjecting it to a washing perfusion with a cold preservation solution and immediately obtaining and processing the samples in order to evaluate them without preserving them.

The parameters evaluated were: production of the superoxide anion free radical (SOA) as an indicator of oxidative stress; and production of the tumour necrosis factor (TNFα), induction of nitric oxide synthase (iNOS) and activation of the NFκB transcriptional factor as markers of inflammatory processes.

Figure 1:
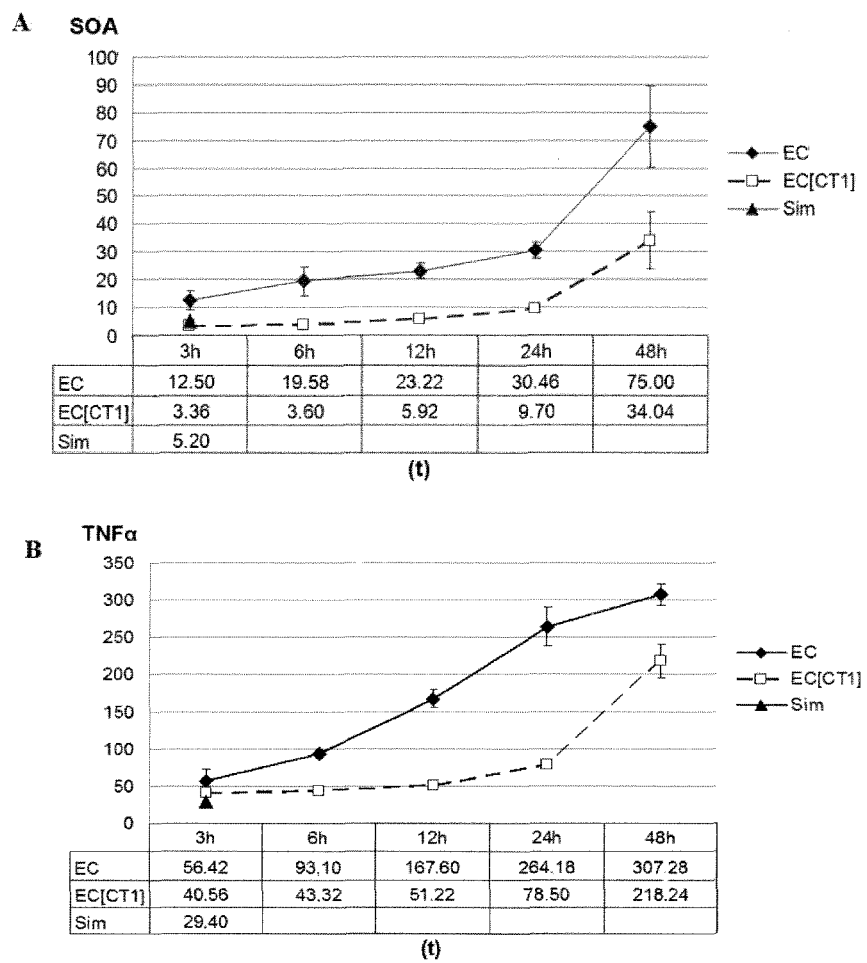
FIG. 1. Comparative study of the effect of cold preservation (4° C.) with the Euro-Collins solution (EC) and the Euro-Collins solution with 0.1 mg/l of CT-1 (EC[CT1]) on Wistar rat kidneys, at different times (t), expressed in hours. A simulated group of rats was also included (Sim). n=5 animals per group. A) Renal levels of the superoxide anion free radical (SOA), expressed in nmol/mg protein/minute. B) Renal levels of tumour necrosis factor alpha (TNFα), expressed in pg/ml. C) Renal levels of inducible nitric oxide synthase (iNOS), expressed in arbitrary units. D) Activation of the NFκB transcriptional factor measured by the levels of renal IκB (IκB), expressed in arbitrary units.
Figure 1:
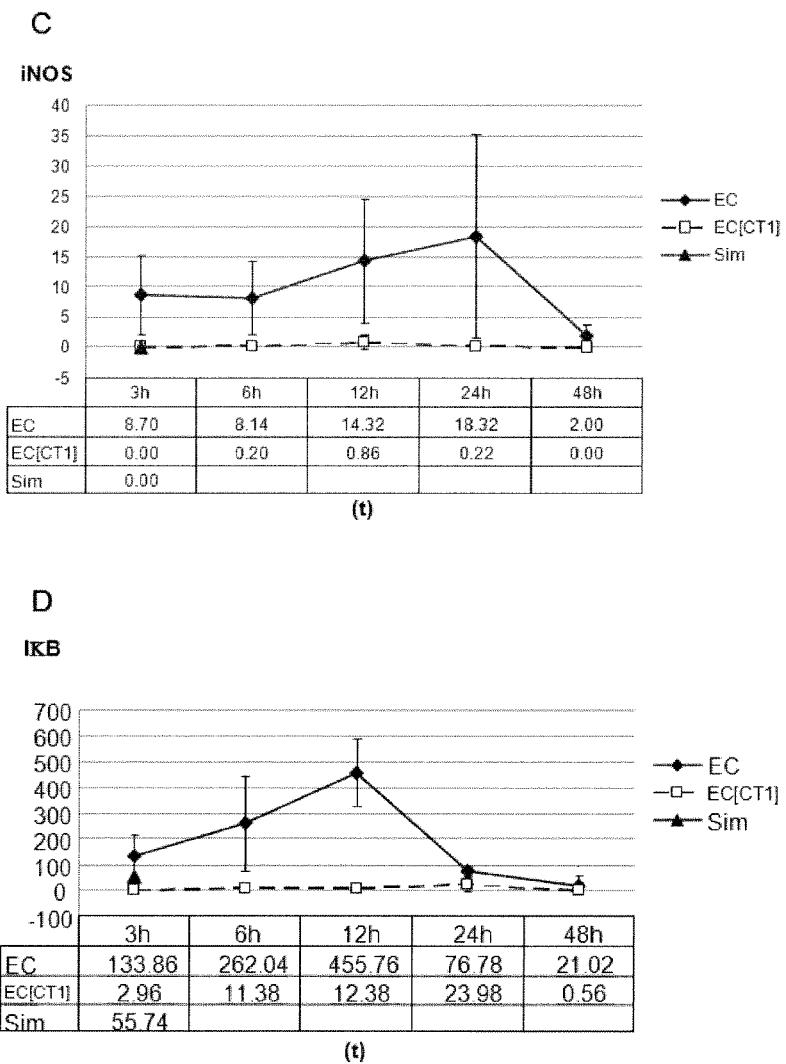

In a first study, the efficacy of CT-1 (0.1 mg/l) was evaluated in a cold preservation composition using the Euro-Collins solution (EC[CT1]) as the base solution, comparing the preservation efficacy in this composition against the preservation in Euro-Collins solution used as the control (EC). The results of the parameters analysed are shown in FIG. 1.

Upon measuring the renal levels of the superoxide anion free radical (SOA), significant differences ($p<0.001$) were observed between the EC and EC[CT1] groups at all times; and also between the Sim and EC[CT1] groups at 48 hours ($p<0.001$) (FIG. 1A). As regards the renal levels of tumour necrosis factor alpha (TNFα), significant differences were observed between the EC and EC[CT1] groups after 6 hours ($p<0.001$); and between the Sim and EC[CT1] groups after 12 hours (12 h: $p<0.05$; after 24 h: $p<0.001$) (FIG. 1B). As regards the renal levels of inducible nitric oxide synthase (iNOS), significant differences were observed between the EC and EC[CT1] groups at all times ($p<0.001$) (FIG. 1C) In the activation of the NFκB transcriptional factor measured by the levels of renal IκB (IκB), significant differences were observed between the EC and EC[CT1] groups at all times (p<0.001); and a significant decrease was also observed in the EC[CT1] group as compared to the Sim group (p<0.001) (FIG. 1D).

Figure 2:
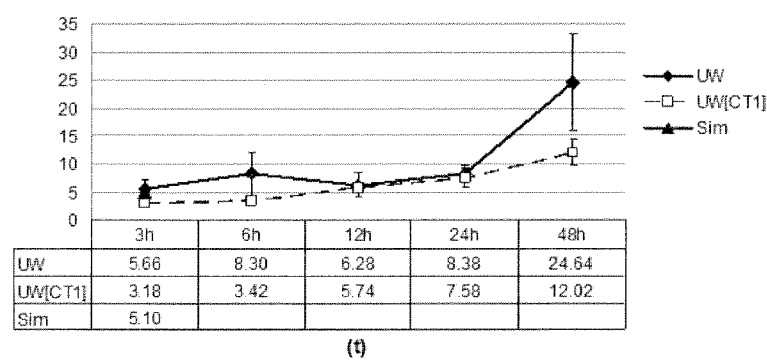
FIG. 2. Comparative study of the effect of cold preservation (4° C.) with the University of Wisconsin solution (UW) and the University of Wisconsin solution with 0.1 mg/l of CT-1 (UW[CT1]) on Wistar rat kidneys, at different times (t), expressed in hours. A simulated group of rats (Sim) was also included. n=5 animals per group. A) Renal levels of the superoxide anion free radical (SOA), expressed in nmol/mg protein/minute. B) Renal levels of tumour necrosis factor alpha (TNFα), expressed in pg/ml. C) Renal levels of inducible nitric oxide synthase (iNOS), expressed in arbitrary units. D) Activation of the NFκB transcriptional factor measured by the levels of renal IκB (IκB), expressed in arbitrary units.
Figure 2:
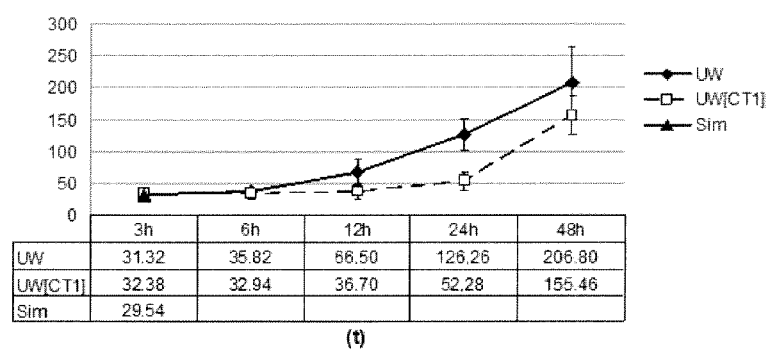
Figure 2:
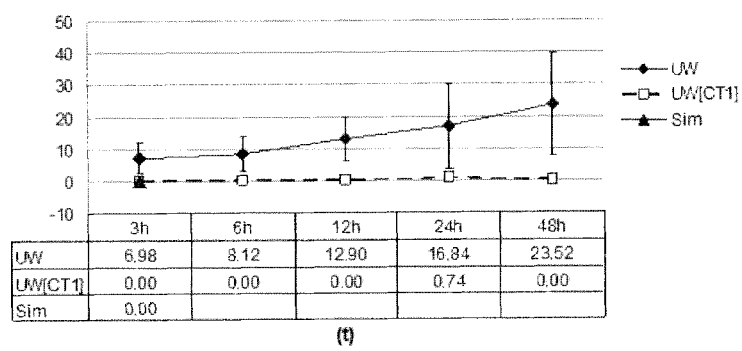
Figure 2:
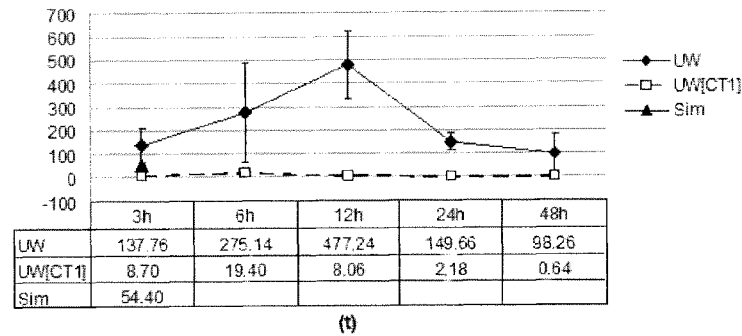

In a second study, the efficacy of CT-1 (0.1 mg/l) was evaluated in a cold preservation composition using the University of Wisconsin solution (UW[CT1]) as the base solution. Similarly, the preservation efficacy in UW[CT1] was compared to the preservation in University of Wisconsin solution (UW) used as a control. The results of the parameters analysed are shown in FIG. 2.

Upon measuring the renal levels of the superoxide anion free radical (SOA), significant differences were observed between the UW and UW[CT1] groups at 48 hours (p<0.05), and also between the UW[CT1] and Sim (p<0.01) groups (FIG. 2A). As regards the renal levels of tumour necrosis factor alpha (TNFα), significant differences were observed between the UW and UW[CT1] groups after 24 hours (p<0.05); between the UW and Sim groups after 12 hours (p<0.05); and also between the UW[CT1] and Sim groups at 48 hours (p<0.001) (FIG. 2B). As regards the renal levels of inducible nitric oxide synthase (iNOS), significant differences were observed between the UW and UW[CT1] groups at all times (p<0.001) (FIG. 2C). In the activation of the NFκB transcriptional factor measured by the renal levels of IκB (IκB), significant differences were observed between the UW and UW[CT1] groups at all times (p<0.001); and also between the UW[CT1] and Sim groups (p<0.01) (FIG. 2D).

Example 3

Study of Cold Renal Preservation With a Cardiotrophin-1 Concentration of 0.2 mg/l Male Wistar rats, 225-250 g/rat, were used. Prior to the extraction, a cold perfusion of the kidney and the liver was performed with the preservation composition at 4° C. Subsequently, during the same surgical action, the two organs were separately extracted. In the first place, the ligaments of the liver were sectioned. Subsequently, the bile duct was sectioned in order to simulate the transplantation donour surgery, and the right renal vein and the right renal artery were ligated. Subsequently, a double ligation of the two ends of the pyloric vein was performed, and it was dessicated. Thereafter, 1 ml of heparinised saline solution was administered by intravenous injection. The aorta was cannulated with a 20G catheter and perfused at a rate of 4 ml/min with 12 ml of the cold preservation composition. Immediately following the perfusion, the inferior vena cava was dissected in order to allow for the exit of the perfusion liquid, and, thereafter, the suprahepatic vena cava and the portal vein were dissected. Following 6 minutes of simultaneous perfusion, the left renal artery and the left renal vein were ligated, the left kidney was extracted and submerged in the preservation composition at 4° C. for a pre-set time. The liver continued to be perfused with 6 additional ml, extracted from its cavity and, finally, also submerged in a container with the cold preservation composition at 4° C. for the pre-set time. Once the pre-established cold preservation time had elapsed, samples were collected in order to be analysed.

A composition in accordance with the invention containing 0.2 mg/l of CT-1 was assayed in University of Wisconsin solution (UW[CT1]) and University of Wisconsin solution was used as the control (UW).

The study included 9 groups of rats:
  4 groups wherein the preservation was performed with UW, with durations of 30 minutes, 3 hours, 24 hours and 48 hours, respectively;
  4 groups wherein the preservation was performed with UW[CT1], with durations of 30 minutes, 3 hours, 24 hours and 48 hours, respectively; and
  1 simulated group (Sim), also without cold preservation, in order to evaluate the baseline values for the different target parameters.

Figure 3:
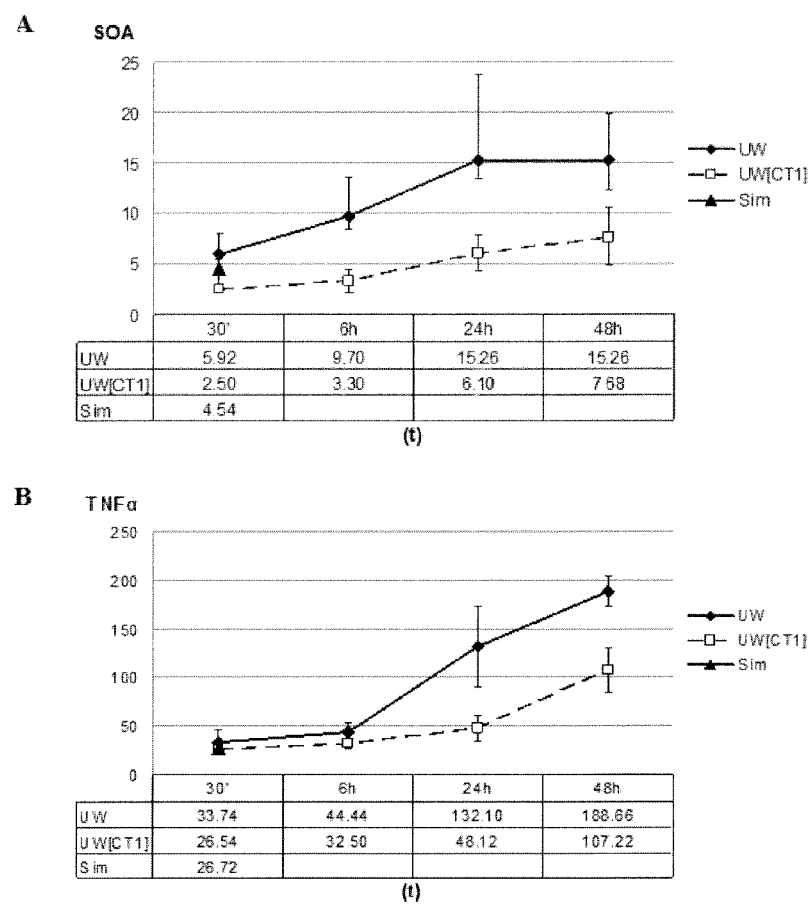
FIG. 3. Comparative study of the effect of cold preservation (4° C.) with the University of Wisconsin solution (UW) and the University of Wisconsin solution with 0.2 mg/l of CT-1 (UW[CT1]) on Wistar rat kidneys, at different preservation times (t): 30 minutes (30'), 6 hours, 24 hours and 48 hours. A simulated group of rats was also included (Sim). n=5 animals per group. A) Renal levels of superoxide anion (SOA), expressed in nmol/mg protein/minute. B) Renal levels of tumour necrosis factor alpha (TNFα), expressed in pg/ml. C) Renal levels of inducible nitric oxide synthase (iNOS), expressed in arbitrary units. D) Activation of the transcriptional factor. Levels of the p65 protein or renal NFκB (NFκB), expressed in arbitrary units. E) Renal levels of the Ser$^{311}$-phosphorylated p65 protein (pNFκB). F) Renal levels of the VCAM-1 vascular adhesion molecule (VCAM-1).
Figure 3:
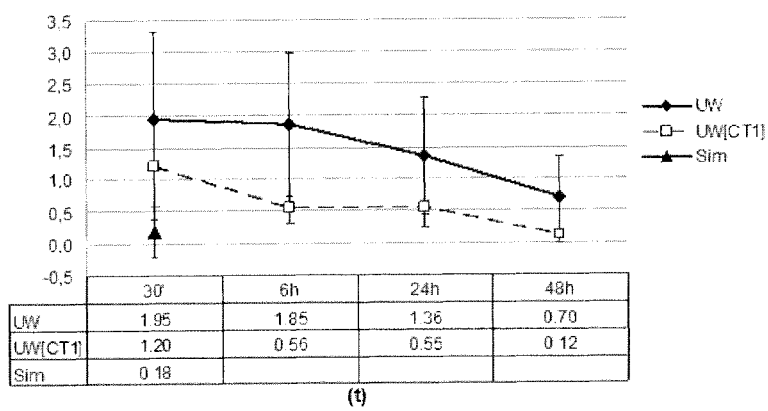
Figure 3:
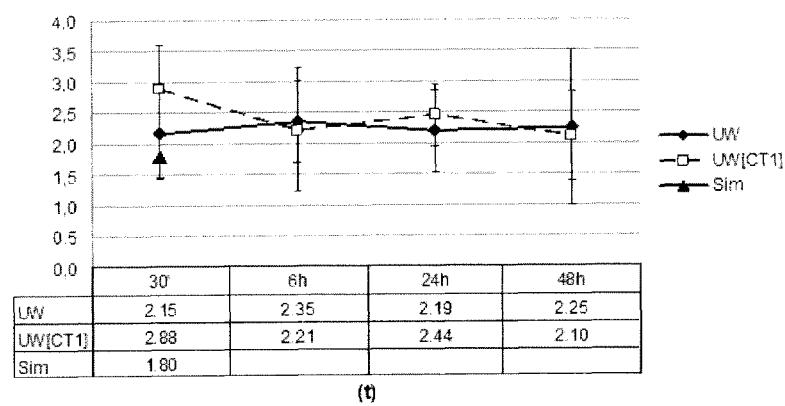
Figure 3:
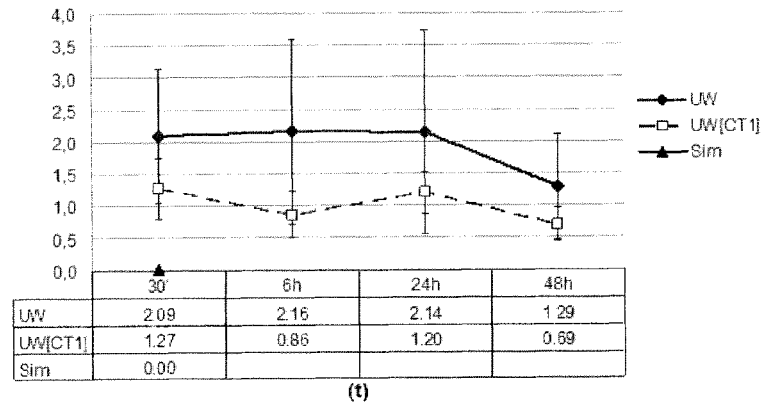
Figure 3:
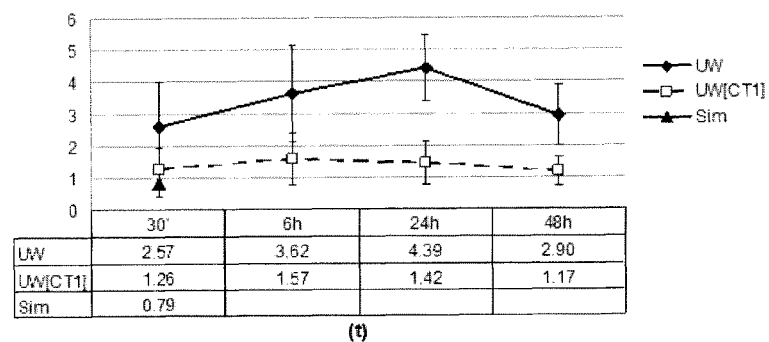

Following the cold preservation for the pre-set time, samples were collected in order to analyse the different target parameters. In this case, the following were evaluated: production of SOA, production of TNFα, induction of iNOS, activation of the NFκB factor and levels of the VCAM-1 vascular adhesion molecule, the latter also being an indicator of inflammatory processes. The results obtained are shown in FIG. 3.

Upon measuring the renal levels of the superoxide anion (SOA), significant differences were observed between the UW and UW[CT1] groups at 6 and 24 hours (p<0.05); and between the Sim and UW groups (p<0.05) (FIG. 3A). As regards the renal levels of tumour necrosis factor alpha (TNFα), significant differences were observed between the UW and UW[CT1] groups at 24 and 48 hours (p<0.05), and also between the Sim and UW groups (p<0.05) (FIG. 3B). As regards the renal levels of inducible nitric oxide synthase (iNOS), significant differences were observed between the UW and UW[CT1] groups at 6 hours (p<0.05); and differences were also observed between the Sim and UW groups (FIG. 3C). With respect to the renal levels of the Ser$^{311}$-phosphorylated p65 protein (pNFκB), significant differences were observed between the UW and UW[CT1] groups at 6 hours; significant differences were also observed between Sim and UW (FIG. 3E). In the renal levels of the VCAM-1 vascular adhesion molecule, significant differences were observed between the UW and UW[CT1] groups at 24 hours (p<0.05); significant differences were also observed between the Sim and UW groups (p<0.05) (FIG. 3F).

Example 4

Study of Cold Renal Preservation and Transplantation With a Composition Having a Cardiotrophin-1 Concentration of 0.1 mg/l The surgical methods were performed following the protocols previously described by Garcia-Criado et al. (J. Interferon Cytokine Res. 2009; 29: 441-450).

The study was performed on male Fischer rats, 225-250 g/rat.

In the first place, in order to obtain the kidney, the donour animal was anaesthesised with a combination of 50 mg/kg ketamine hydrochlorhydrate (Ketolar, Parke-Davis), 50 mg/kg diazepam (Valium. Roche) and 25 mg/kg atropine (Atropina, Braun). The animals were placed on a thermostated surface and, following identification and direction of the kidney, a small portion of perirenal and periureteral fat was preserved in order to facilitate handling. The ureter was sectioned and cannulated with a plastic tube (0.68 mm OD, 0.28 mm ID, ref. 427400, Intramedic, Clay Adams). At this time, the rat was administered heparin (1,000 IU) and, with the heart beating, the kidney was perfused with the cold preservation composition to be assayed, at 4° C. and a rate of 0.74 ml/min for 150 seconds. Thereafter, the renal artery and the renal vein were cut and a polyethylene tube (1.57 mm OD, 1.14 mm ID, ref. 427430, IntramedicR-Clay Adams) was inserted in the renal vein.

Once the kidney was extracted, it was kept in the cold preservation composition (4° C.) for 24 hours.

Finally, the transplantation per se was performed. The recipient rat was anaesthesised as previously described. Following the laparotomy, the left kidney was extracted, the preserved kidney was washed and orthotopically placed in the recipient rat, and an anastomosis of the renal arteries was performed using a polyamide monofilament thread. The donour's and recipient's veins and ureters were anastonnosised using the plastic tubes previously placed in the donour kidney. The peritoneum and the abdominal muscle were closed in a single plane with vicryl 5/0 continuous suture. The skin was closed with staples. The anastomosis-re-perfusion did not last more than 10 min, and the total in the recipient rat did not exceed 30 minutes. The animal was kept warm by means of an incandescence lamp until its movement and reactions were normal.

Once the transplantation was completed, blood re-perfusion was maintained for a pre-set time, after which time blood, urine and kidney samples were collected.

The pre-set re-perfusion times for the different groups were, respectively, in days t(d): 1, 3, 7 and 14. Moreover, a simulated group of rats was included (Sim).

A composition in accordance with the invention that contained 0.1 mg/l of CT-1 was assayed in University of Wisconsin solution (UW[CT1]) and University of Wisconsin solution used as the control (UW).

The study included 11 groups of rats (for all the groups, n>15 transplantations):
  5 groups wherein the kidney preservation was performed with UW, the re-perfusion time varying in each group (1, 3, 7, 14 and 30 days, respectively);
  5 groups wherein the preservation was performed with UW[CT1 ], the re-perfusion time also varying; and
  1 simulated group (Sim), wherein the kidney was extracted from each donour rat as described above, but, following washing with the cold preservation solution (UW), was immediately transplanted.

The following were analysed in this study: survival time of the transplantation recipient rats; production of SOA and TNFα, IL-6, and the soluble forms of the sICAM-1 and sVCAM-1 intercellular adhesion molecules; activation of NFκB; and, as indicators of renal function, serum levels of creatinine and creatinine clearance.

The results obtained are shown in FIG. 4.

As regards survival, significant differences were observed from day 5 between the UW and UW[CT1] groups ($p<0.01$) and between the UW and Sim groups ($p<0.001$) (FIG. 4A). Upon measuring the serum levels of creatinine (CREAT), significant differences were observed between the UW and UW[CT1] groups at all times ($p<0.05$), and also between the UW and Sim ($p<0.01$) groups (FIG. 4B). As regards the levels of creatinine clearance (CRCL), significant differences were observed between the UW and UW[CT1] groups at all times ($p<0.01$), and also between the UW and Sim groups ($p<0.01$) (FIG. 4C). As regards the renal levels of the superoxide anion free radical (SCA), significant differences were observed between the UW and UW[CT1] groups at all times ($p<0.001$), and also between the UW and Sim groups ($p<0,001$) (FIG. 4D). For the renal levels of tumour necrosis factor alpha (TNFα), significant differences were observed between the UW and UW[CT1] groups at all times ($p<0.01$), and also between the UW and Sim groups ($p<0.01$) (FIG. 4E). For the renal levels of interleukin-6 (IL-6), significant differences were observed between the UW and UW[CT1] groups at all times ($p<0.05$), and between the UW and Sim groups at 3 days ($p<0.01$) (FIG. 4F). As regards the activation of the NFκB transcriptional factor measured by the renal levels of IκB (IκB), significant differences were observed between the UW and UW[CT1] groups at all times ($p<0.01$), and also between the UW and Sim groups ($p<0.01$) (FIG. 4G). With respect to the levels of the soluble form of the ICAM-1 adhesion molecule (sICAM-1), significant differences were observed between the UW and UW[CT1] groups at all times ($p<0.01$), and also between the UW and Sim groups ($p<0.01$) (FIG. 4H). As regards the levels of the soluble form of the VCAM-1 adhesion molecule (sVCAM-1), significant differences were observed between the UW and UW[CT1] groups at all times ($p<0.01$), and also between the UW and Sim groups ($p<0.01$) (FIG. 4I).

Example 5

Study of Cold Lung and Heart Preservation With a Cardiotrophin 1 Concentration of 0.2 mg/L The study was conducted in male Wistar rats (280-320 g). They were anesthetized with intraperitoneal thiopental (30 mg/kg), a tracheotomy was performed and the trachea was intubated. They were connected to a rodent ventilator (Harvard instrument, MA. USA) and ventilated with ambient air. They were administered 50 IU of heparin through the penile vein and laparoscopic sternotomy was performed 5 minutes later. The thoracic vena cave was cut and the lung was perfused through the pulmonary artery with 20 ml of cold Wisconsin solution at a pressure of 20 cm of water. After inflating the lungs and ligating the trachea, the heart-lung block was separated from the animal and placed in a container with 40 ml of Wisconsin solution, keeping it at 4° C. for 0, 24 and 48 hours. Once that time elapsed, the heart and lung were separated, weighed and frozen in liquid nitrogen. Cardiotrophin-1 at a concentration of 0.2 μg/ml was added to the preservation liquid in half the animals of each time (n=5).

The experimental groups would therefore be:
1. Time 0-control: once perfused with Wisconsin without CT-1, the organs are frozen immediately (N=5).
2. Time 0-CT-1: once perfused with Wisconsin with CT-1, the organs are frozen immediately (N=5).
3. Time 24 h-control: once perfused with Wisconsin without CT-1, the organs are preserved in Wisconsin without CT-1 for 24 h (N=5).
4. Time 24 h-CT-1: once perfused with Wisconsin with CT-1, the organs are preserved in Wisconsin with CT-1 for 24 h (N=5).
5. Time 48 h -Control: once perfused with Wisconsin without CT-1, the organs are preserved in Wisconsin without CT-1 for 48 h (N=5).
6. Time 48 h-CT-1 once perfused with Wisconsin with CT-1, the organs are preserved in Wisconsin with CT-1 for 48 h (N=5).

The cardiotrophin used was rat CT-1.

After the cold preservation for the pre-established time, the samples for analyzing the various target parameters were prepared and analyzed. The frozen lungs and heart were homogenized in 5 volumes of tris-HCl buffer (50 mM, pH 7.4) at 4° C. (also containing 0.50 ml/l of Triton X-100) for 2 minutes at 13,000 rpm with an Ultra-Turrax T25 homogenizer (IKA, Staufen). After centrifuging, the supernatant was obtained, and the protein concentration therein was measured using the Lowry method. In this case, NOS induction, p65 NFκB levels, pNFκB levels and SOA production were evaluated for the lung. iNOS induction, p65 NFκB levels, ICAM levels, SOA production and TNFα production were evaluated for the heart.

The antibodies used in this case are from different companies from those used in the previous experiments and they are:

Anti-α-Tubulin (Cell Signaling, 2144) (loading control)
Anti-iNOS/NOS Type II (S-20) (Santa Cruz, Biotechnology, sc-651)
Anti-NFκB (Cell Signaling, NFκB p65, 9242)
Anti-pNFκB (Cell Signaling, p-NFκB p65, 3031)
Anti-ICAM-1 (Labgen, CTS 11333)
Activated anti-caspase3 (Asp-175) (Cell Signaling, 9661)

FIG. 5A shows that the preservation with Wisconsin without CT-1 for 24, and even more so, for 48 hours induces an increase in the expression of inducible nitric oxide synthase (iNOS) in rat lungs (tubulin-corrected). This increase is not observed when they are preserved with Wisconsin with CT-1.

FIG. 5B shows that the preservation with Wisconsin without CT-1 for 24 and 48 hours induces a minor increase in the expression of p65 NFκB in rat lungs. This increase is not observed when they are preserved with Wisconsin with CT-1.

FIG. 5C shows that the preservation with Wisconsin without CT-1 for 24 and 48 hours induces a significant increase in phospho-p65 NFκB (p NFκB) tissue levels. This increase is not observed when the lungs are preserved with Wisconsin with CT-1.

FIG. 5D shows that the preservation of the rat lungs with Wisconsin without CT-1 for 24 and 48 hours induces a significant increase in the superoxide anion concentration. This increase is much smaller when they are preserved with Wisconsin containing CT-1.

FIG. 6A shows that the preservation with Wisconsin without CT-1 for 24, and even more so, for 48 hours induces an increase in the expression of inducible nitric oxide synthase (tubulin-corrected) in rat heart. This increase was not different when they were preserved with University of Wisconsin solution containing CT-1.

FIG. 6B shows that the preservation with Wisconsin without CT-1 for 48 hours induces an increase in the expression of p65 NFκB in rat heart. This increase was not observed when they were preserved with Wisconsin containing CT-1.

FIG. 6C shows that the preservation with Wisconsin without CT-1 for 24 and 48 hours induces a significant increase in ICAM-1 tissue levels in rat heart. This increase is similar when they are preserved with Wisconsin containing CT-1.

FIG. 6D shows that the preservation with Wisconsin without CT-1 for 24 and 48 hours induces a significant increase in the superoxide anion (SOA) concentration in rat heart. This increase is significantly less when they are preserved with Wisconsin containing CT-1.

Figure 7:
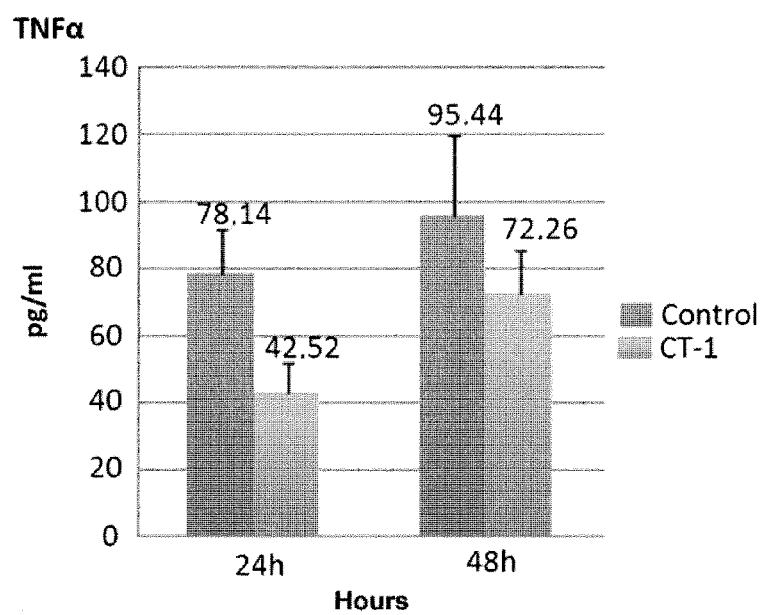
FIG. 7. Comparative study of the effect of the cold preservation (4° C.) in the lung-heart block of Wistar rats of the University of Wisconsin solution (S/CT-1) and the University of Wisconsin solution with 0.2 mg/L of CT-1 (C/CT-1) at different times expressed in hours over the tumor necrosis factor-alpha (TNFα) concentration in the preservation liquid, expressed in pg/mL. n=5 animals per group.
Figure 8:
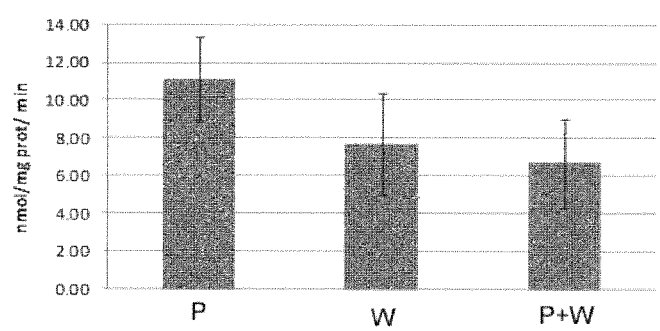
FIG. 8. Comparative study of the effect of the cold preservation (4° C.) for 24 and 48 hours in the kidneys of Wistar rats of the University of Wisconsin (UW) solution containing 0.2 mg/L of CT-1 only in the preservation solution (P), only in the washing solution (W) or in both preservation and washing solutions (P+W). n=5 animals per group. A) and G): Superoxide anion (SOA) free radical kidney levels at 24 and 48 hours, respectively, expressed in nmol/mg protein/minute. B) and H): Tumor necrosis factor-alpha (TNFα) concentration in the preservation liquid at 24 and 48 hours, respectively, expressed in pg/mL. C) and I): Tubulin-corrected inducible nitric oxide synthase (iNOS) kidney levels at 24 and 48 hours, respectively, expressed in arbitrary units. D) and J): Tubulin-corrected soluble ICAM-1 adhesion molecule (ICAM-1) kidney levels at 24 and 48 hours, respectively, expressed in arbitrary units. E) and K): Renal activation of tubulin-corrected NFκB transcription factor measured as IκB (IκB) tissue levels at 24 and 48 hours, respectively, expressed in arbitrary units. F) and L): Activation of the renal NFκB transcription factor measured as tubulin-corrected Ser$^{311}$-phosphorylated p65 protein (phosphop65) tissue levels at 24 and 48 hours, respectively, expressed in arbitrary units. Arbitrary units (AU).
Figure 8:
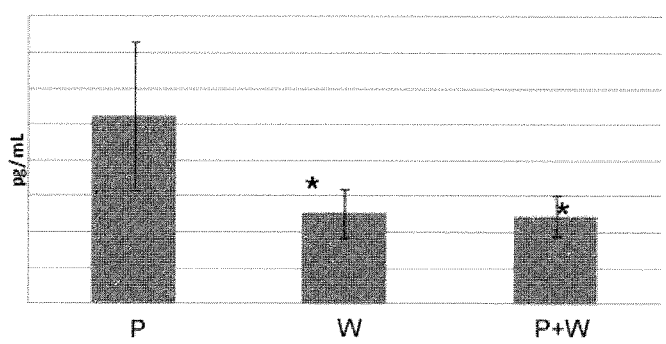
Figure 8:
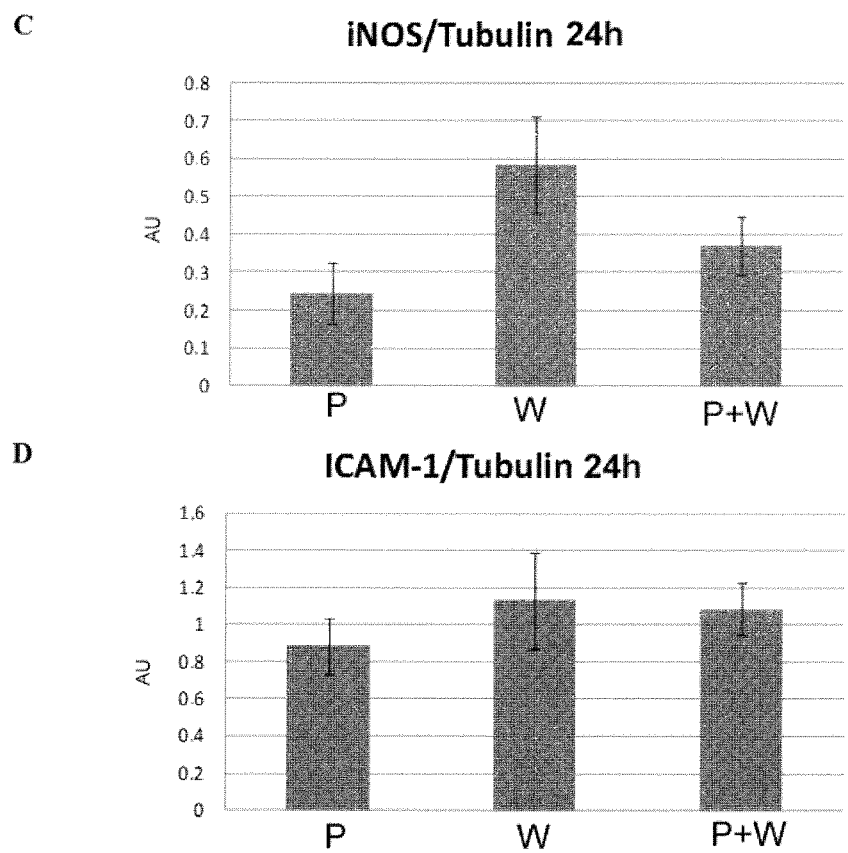
Figure 8:
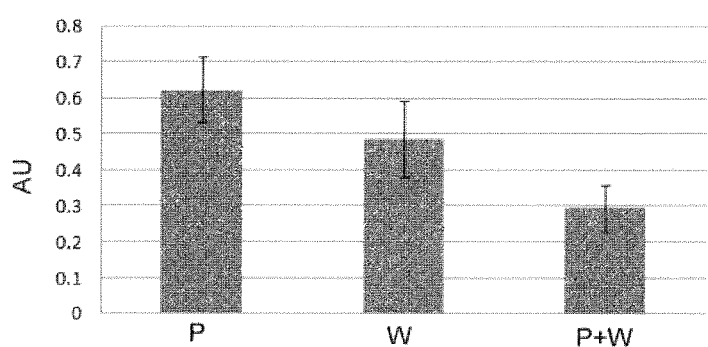
Figure 8:
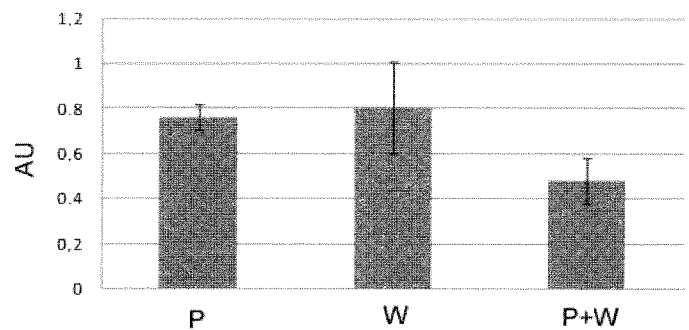
Figure 8:
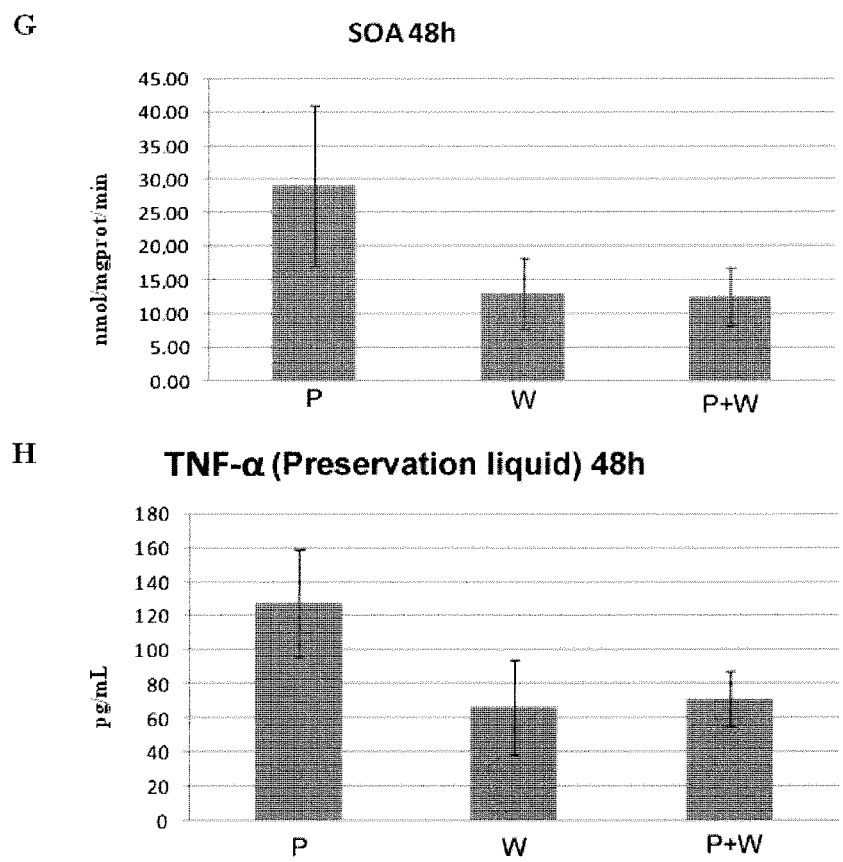
Figure 8:
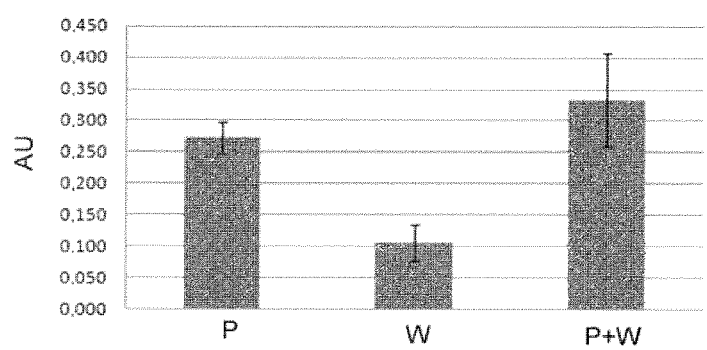
Figure 8:
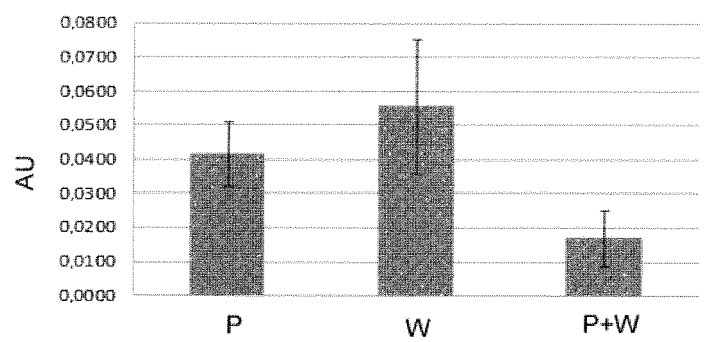
Figure 8:
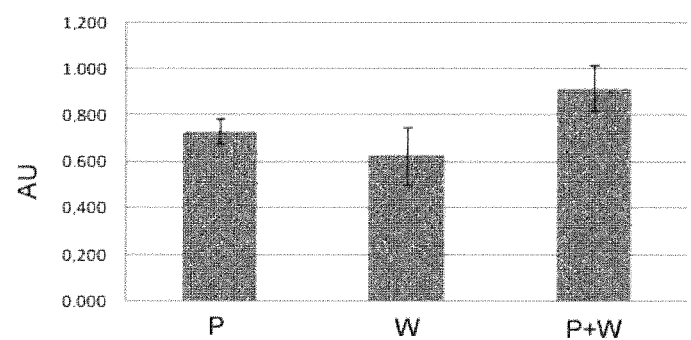
Figure 8:
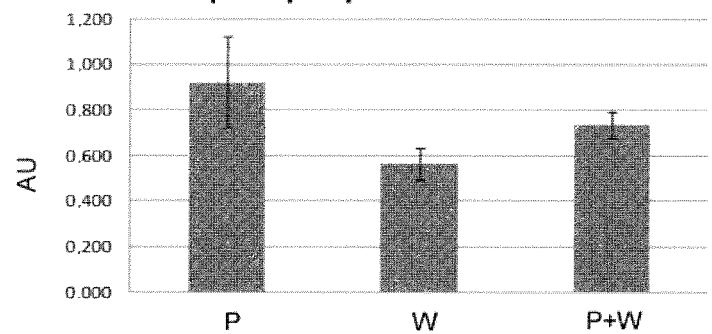

FIG. 7 shows that when CT-1 is added to the preservation liquid (University of Wisconsin solution), the amount of TNF-α found in the preservation liquid is less than when CT-1 is not added. This is observed at both 24 and 48 hours of preservation (TNF-α is not detected in the preservation liquid at time 0).

Example 6

Comparison of the Protective Effect of Cardiotrophin 1 in the Washing Liquid, the Preservation Liquid or in Both on the Cold Preservation-Induced Renal Damage With a Cardiotrophin 1 Concentration of 0.2 mg/L Wistar rats (males 225-250 g/rat) were used. The rats were anesthetized by means of intraperitoneal injection with ketamine chloride (75 mg/kg)+diazepam (50 mg/kg) and atropine (20 mg/kg). A median laparotomy was performed and the retroperitoneum was dissected to expose the abdominal aorta and the renal arteries to the aortic bifurcation (iliac arteries). The renal vessels were subsequently dissected by means of ligating the inferior suprarenal artery and gonadal artery branches; and the ureter was dissected in its proximal half, maintaining the periureteral fat.

The aorta was then clamped under the exit from the renal artery, thereby maintaining vascularization, for perfusing the organ (washing perfusion W). The aortic catheterization was performed by means of transverse aortotomy on the anterior face, after distal ligation at the height of bifurcation. The aorta was occluded by means of ligation above the left renal artery once the clamp was removed to start cold perfusion (4° C.) with the cold organ preservation composition (University of Wisconsin (UW) solution with or without CT-1, and with 1 mg/Kg of sodium heparin). Drainage was done through the renal vein, which was sectioned at its junction with the vena cava. Once the kidney was perfused, it was separated by sectioning the aorta and ureter and was immersed in 20 ml of the preservation solution (University of Wisconsin (UW) solution with or without CT-1 0.2 mg/L, and with 0.25 mg/L of sodium heparin). The kidney was maintained in the preservation liquid for 24 or 48 hours. The study groups were 6:

1—Group P-24 h: Preservation for 24 hours with CT-1 in the preservation solution but not in the washing solution.
2—Group W-24 h: Preservation for 24 hours with CT-1 in the washing solution but not in the preservation solution.
3—Group P+W-24 h: Preservation for 24 hours with CT-1 in the preservation solution and in the washing solution.
4—Group P-48 h: Preservation for 48 hours with CT-1 in the preservation solution but not in the washing solution.
5—Group W-48 h: Preservation for 48 hours with CT-1 in the washing solution but not in the preservation solution.
6—Group P+W-48 h: Preservation for 48 hours with CT-1 in the preservation solution and in the washing solution.

Each group consisted of 5 animals.

Once the preservation time had elapsed, the kidney was removed from the preservation medium, washed with cold saline and immediately frozen in liquid nitrogen.

The evaluated parameters were: superoxide anion (SOA) free radical production as an indicator of oxidative stress; and tumor necrosis factor (TNFα) production, inducible nitric oxide synthase (iNOS) and ICAM-1 adhesion molecule tissue levels, and NFκB transcription factor activation (measured as of phospho-p65 and IκB tissue levels) as preservation-induced inflammatory process markers in the kidney.

Sample preparation and analysis as well as the methods for determining SOA, TNFα, iNOS, ICAM-1 and NFκB activation have been described in the Materials and Methods section.

The results obtained when preservation was performed for 24 hours were the following:

Although the SOA tissue levels were lower when CT-1 was added to the washing liquid and to the preservation liquid, no significant differences were found when CT-1 was added only in the preservation liquid (P), only in the washing liquid (W) or in both (P+W) (FIG. 8A).

When CT-1 was placed in the washing liquid (W) or in the preservation and washing liquid (P+W), the TNFα levels in the preservation liquid were significantly less than when CT-1 was placed only in the preservation liquid (P) (FIG. 8B), without significant differences between these two groups.

There are no significant differences in the iNOS (tubulin-corrected) levels in the renal tissue when CT-1 is placed only in the preservation liquid (P), only in the washing liquid (W) or in both (P+W) (FIG. 8C).

No significant differences were observed in 1CAM-1 adhesion molecule (tubulin-corrected) levels in renal tissue when CT-1 was placed only in the preservation liquid (P), only in the washing liquid (W) or in both (P+W) (FIG. 8D). No significant differences were observed in NFκB transcription factor renal activation (measured as IκB tissue levels) when CT-1 was placed only in the preservation liquid (P), only in the washing liquid (W) or in both (P+W) (FIG. 8E).

Nor were significant differences observed in NFκB transcription factor renal activation (measured as phospho-p65 tissue levels) when CT-1 was placed only in the preservation liquid (P), only in the washing liquid (W) or in both (P+W) (FIG. 8F).

The results obtained when the preservation was performed for 48 hours were the following:

It was observed that when CT-1 was placed in the preservation solution and in the washing solution (P+W). SOA tissue levels were lower than when it was placed only in the preservation liquid (P), but not different from when it was added only to the washing liquid (W) (FIG. 8G).

When CT-1 was placed in the preservation solution and in the washing solution (P+W). TNF-α levels in the perfusion liquid were lower than when it was placed only in the preservation liquid (P), but not different from when it was placed only in the washing liquid (W) (FIG. 8H).

When CT-1 was placed in the preservation solution and in the washing solution (P+W), iNOS (tubulin-corrected) tissue levels were lower than when it was placed only in the preservation liquid (P) or only in the washing liquid (W), but they were not significantly different (FIG. 8I).

There were no significant differences in iCAM (tubulin-corrected) tissue levels when CT-1 was placed only in the preservation liquid (P), only in the washing liquid (W), or in the preservation liquid and washing liquid (P+W) (FIG. 8J). No significant differences were observed in NFκB transcription factor renal activation (measured as IκB tissue levels) when CT-1 was placed only in the preservation liquid (P), only in the washing liquid (W) or in both (P+W) (FIG. 8K).

There were no significant differences in NFκB transcription factor renal activation (measured as phospho-p65 tissue levels) when CT-1 was placed only in the preservation liquid (P), only in the washing liquid (W), or in both (P+W) (FIG. 8L).

It is important to point out that even though this study did not include a control group in which preservation liquid and washing liquid without CT-1 were used, the data obtained in comparable previous experiments in which said control was included indicate that in all the analyzed groups (CT-1 only in the preservation liquid (P), only in the washing liquid (W) or in both (P+W)), the SOA, iNOS (tubulin-corrected), ICAM (tubulin-corrected), IκB and phospho-p65 tissue levels, as well as TNF-α levels in the perfusion liquid, were always much lower than those observed in said control group, demonstrating the antioxidant and anti-inflammatory effect of CT-1 used in any of the three conditions described.

CONCLUSIONS

From the above studies it may be concluded, in the first place, that the addition of CT-1 to the cold organ preservation solution used for transplantation, be it Euro-Collins or University of Wisconsin solution, reduces the production of oxygen free radicals for the preserved kidney, particularly when the latter has been subjected to very long preservation times (24-48 hours). Since the Euro-Collins and UW preservation solutions have a very different composition, it is reasonable to assume that CT-1 will be equally effective with other cold preservation solutions.

In the second place, the protective effect of CT-1 is more evident when the kidneys have been preserved using Euro-Collins as the base solution, possibly due to the lower performance that the latter provides in the cold preservation of kidneys. However, in the assays performed, the best results, for both cold preservation and re-perfusion, were obtained when the UW solution with CT-1 was used.

Finally, when the preserved kidney is transplanted into a syngeneic rat, the addition of CT-1 to the cold preservation solution improves the animal's survival, renal function, histological damage, oxidative stress, production of pro-inflammatory cytokines, induction of iNOS, infiltration of neutrophiles and activation of the NFκB transcriptional factor, as compared to those kidneys that have been preserved in a cold preservation solution without CT-1.

In sum, we may state that the addition of CT-1 to the cold preservation solution prevents and reduces the damage caused by cold ischaemia and the damage caused by ischaemia/post-transplantation re-perfusion that causes acute tubular necrosis in the kidney, thereby improving renal functions and survival.

In addition, with respect to the lung-heart block, the experiments allow concluding that adding CT-1 to the cold preservation solution of the lung-heart block produces lower NFκB activation and lower superoxide anion (SOA) production both in the heart and lung, as well as lower TNF-α release into the preservation liquid, which demonstrates that there is lower induction of ischemia and cold preservation-stimulated oxidative and inflammatory processes.

In the case of the lung, it is further observed that the addition of CT-1 to the cold preservation solution produces lower iNOS induction.

Finally, in the experimental renal preservation model with University of Wisconsin cold preservation solution in rats it has been found that adding CT-1 only in the kidney washing liquid does not produce worse results in terms of factors relating to the antioxidant and anti-inflammatory effect measured than adding CT-1 to both the washing liquid and the preservation liquid does. This would allow greatly simplifying the handling of CT-1 for the organ preservation process and significantly reducing the potential exposure of the recipient to CT-1.

The invention claimed is:

1. A method for the cold preservation of an organ which comprises contacting said organ with a cold organ preservation composition that comprises:
cardiotrophin-1 and
a cold organ preservation solution at a temperature of between 0° C. and 25° C., thereby cold preserving the organ, wherein the organ is a kidney and wherein the kidney is isolated by extraction from a live or dead donor, or is in a live or dead donor.

2. The method according to claim 1, wherein the organ is isolated.

3. The method according to claim 2, wherein the composition is contacted with the isolated organ extracted from the dead donor by means of perfusion and after said perfusion, by means of immersion.

4. The method according to claim 2, wherein the composition is contacted with the isolated organ extracted from the dead donor by means of perfusion and after said perfusion, it is not maintained immersed in said composition.

5. The method according to claim 1, wherein said composition is contacted with the organ by washing, immersion, perfusion or a combination thereof.

6. The method according to claim 5, wherein the composition is contacted with the organ by means of perfusion in the dead donor and by means of immersion after the extraction.

7. The method according to claim 5, wherein the composition is contacted with the organ by means of perfusion in the dead donor.

8. The method according to claim 1, wherein the cold organ preservation composition is at a temperature of approximately 4° C.

9. The method according to claim 1, wherein the cold organ preservation solution further comprises:
(a) at least one buffer agent
(b) at least one impermeating agent and
(c) at least one electrolyte.

10. The method according to claim 9, wherein the buffer agent is selected from the group consisting of phosphate, bicarbonate, sulfate, histidine, histidine-HCl, HEPES, citrate and a combination thereof; the impermeating agent is selected from the group consisting of histidine, glucose, sucrose, mannitol, trehalose, gluconate, citrate, lactobionate, raffinose and a combination thereof; and/or the electrolyte is selected from the group consisting of sodium, potassium, magnesium, calcium, chloride and a combination thereof.

11. The method according to claim 1, wherein the cold organ preservation solution additionally comprises at least one colloid agent, at least one metabolic agent, at least one amino acid, at least one antioxidant agent, at lest one vitamin and/or at least one antibiotic.

12. The method according to claim 11, wherein the at least one colloid agent is selected from the group consisting of hydroxyethyl starch (HES), polyethylene glycol of a combination of both.

13. The method according to claim 1, wherein the cold organ preservation solution is selected from the group consisting of Euro-Collins solution (EC), the University of Wisconsin solution (UW), the Institut Georges Lopez solution (IGL-1), the Celsior solution (CEL), the Kyoto solution (ET-Kyoto), the Polysol solution, the Bretschneider or histidine-tryptophan-ketoglutarate solution (HTK), the Marshall's solution (HOC or hyperosmolar citrate), the Perfadex solution, the St. Thomas Hospital solutions 1 and 2 (STH-1, STH-2), the Lyon preservation solution (LYPS), the Stanford solution (STF) and the modified UW-gluconate solution (Belzer MPS).

14. The method according to claim 1, wherein the cold organ preservation solution is selected from the group consisting of:
(i) a solution comprising glucose, chlorine, potassium, sodium, $K_2HPO_4$, $KH_2PO_4$ and $NaHCO_3$
(ii) a solution comprising lactiobionate, raffinose and HES
(iii) a solution comprising lactiobionate, raffinose and polyethylene glycol
(iv) a solution comprising lactiobionate, raffinose and mannitol
(v) a solution comprising gluconate, trehalose and HES
(vi) a solution comprising gluconate, trehalose and polyethylene glycol
(vii) a solution comprising histidine and mannitol and
(viii) a solution comprising citrate and mannitol.

15. The method according to claim 1, wherein cardiotrophin-1 is added to the cold organ preservation solution just prior to contacting the organ with said composition.

* * * * *